US012806391B2

(12) United States Patent
Shi et al.

(10) Patent No.: US 12,806,391 B2
(45) Date of Patent: Nov. 24, 2026

(54) MICRO-ELECTROPORATION BASED DRUG DELIVERY SYSTEM, METHODS FOR USE AND FABRICATION THEREOF

(71) Applicant: City University of Hong Kong, Hong Kong (CN)

(72) Inventors: Peng Shi, Hong Kong (CN); Yuan Wang, Hong Kong (CN); Jin Qu, Hong Kong (CN); Kai Xie, Hong Kong (CN); Suling Duan, Hong Kong (CN); Xingdao He, Hong Kong (CN)

(73) Assignee: City University of Hong Kong, Hong Kong (CN)

( * ) Notice: Subject to any disclaimer, the term of this patent is extended or adjusted under 35 U.S.C. 154(b) by 956 days.

(21) Appl. No.: 17/804,118

(22) Filed: May 26, 2022

(65) Prior Publication Data

US 2023/0381476 A1 Nov. 30, 2023

(51) Int. Cl.
*A61M 37/00* (2006.01)
*A61N 1/32* (2006.01)

(52) U.S. Cl.
CPC ......... *A61M 37/0015* (2013.01); *A61N 1/327* (2013.01); *A61M 2037/0007* (2013.01); *A61M 2037/0023* (2013.01); *A61M 2037/0053* (2013.01); *A61M 2037/0061* (2013.01); *A61M 2202/07* (2013.01); *A61M 2202/30* (2013.01)

(58) Field of Classification Search
CPC ...... A61M 37/0015; A61M 2037/0046; A61M 2037/0007; A61M 2037/0023; A61M 2037/0053; A61M 2037/0061; A61N 1/327
See application file for complete search history.

(56) References Cited

U.S. PATENT DOCUMENTS 5,693,622 A * 12/1997 Wolff ........................ B82Y 5/00 514/44 R
6,219,574 B1 4/2001 Theeuwes et al.
8,911,749 B2 12/2014 Klemm et al.
10,010,499 B2 7/2018 Chiang et al.
2002/0020688 A1* 2/2002 Sherman ................... B26F 1/24 216/2
2002/0082543 A1* 6/2002 Park .................. A61M 37/0015 604/20

(Continued)

OTHER PUBLICATIONS

Bao, L., Park, J., Bonfante, G., & Kim, B. (2022). Recent advances in porous microneedles: materials, fabrication, and transdermal applications. Drug delivery and translational research, 12(2), 395-414. (Year: 2021).*

(Continued)

*Primary Examiner* — Nilay J Shah
(74) *Attorney, Agent, or Firm* — S&F/WEHRW

(57) ABSTRACT

An electricity-driven, micro-electroporation based drug delivery system, in particular, an electrically conductive array of microprotrusions containing intended substances or molecules to be delivered, which is to the benefit of a recipient receiving vaccination transcutaneously in the absence of any assistive mechanical or actuation device as in conventional injection methods, so as to lower safety risks, improve immunization efficiency, and also induce immune response of the recipient more effectively at a relatively lower dose of vaccines.

20 Claims, 21 Drawing Sheets
(4 of 21 Drawing Sheet(s) Filed in Color)

(56) References Cited

U.S. PATENT DOCUMENTS

| | | | | |
|---|---|---|---|---|
| 2008/0033338 | A1* | 2/2008 | Smith | A61N 1/0444 604/20 |
| 2010/0137779 | A1* | 6/2010 | Seitz | A61N 1/30 335/229 |
| 2015/0141910 | A1* | 5/2015 | Francis | A61M 37/0015 264/255 |
| 2016/0230197 | A1* | 8/2016 | Milleret | C25B 3/295 |
| 2018/0344997 | A1* | 12/2018 | Han | A61K 9/06 |
| 2019/0329035 | A1* | 10/2019 | Park | A61N 1/36034 |
| 2021/0346665 | A1* | 11/2021 | Xu | A61K 45/06 |

OTHER PUBLICATIONS

Rouphael, et.al., "The safety, immunogenicity, and acceptability of inactivated influenza vaccine delivered by croneedle batch (TIV-MNP 2015): a randomised, partly blinded, placebo-controlled, phase 1 trial" Lancet 2017, vol. 390, Jun. 27, 2017, p. 649-58.

Xia, et. al., "An ultra-low-cost electroporator with microneedle electrodes (ePatch) for SARS-CoV-2 vaccination", PNAS 2021 vol. 118 No. 45, Apr. 27, 2022.

Kusama, et. al., "Transdermal electroosmotic flow generated by a porous microneedle array patch", Nature Communications, 2021, 12:658.

Glenn, et. al., "Transcutaneous immunization: A human vaccine delivery strategy using a patch", Nature Medicine, vol. 6, No. 12, Dec 2000, p. 1403-6.

Gill, et. al., "Cutaneous vaccination using microneedles coated with hepatitis C DNA vaccine", Gene Therapy (2010) 17, 811-814.

Brace, et. al., "Plasmid DNA vaccination using skin electroporation promotes poly-functional CD4 T-cell responses", Immunology and Cell Biology, 2011, 89, 492-496.

Wang, et. al., "High-Efficiency Cellular Reprogramming by Nanoscale Puncturing", Nano Lett. 2020, 20, 5473-5481.

Tran, et. al., "Transdermal microneedles for the programmable burst release of multiple vaccine payloads", Nature Biomedical Engineering, vol. 5, Sep. 2021, 998-1007.

Qu, et. al., "Injectable antibacterial conductive hydrogels with dual response to an electric field and pH for localized "smart" drug release", Acta Biomaterialia 72, 2018, 55-69.

Li, et. al., "A facile approach to enhance antigen response for personalized cancer vaccination", Nature Materials, vol. 17, Jun. 2018, 528-534.

Wang, et. al., "Enhanced Cancer Immunotherapy by Microneedle Patch-Assisted Delivery of Anti-PD1 Antibody", Nano Lett. 2016, 16, 2334-2340.

* cited by examiner

MICRO-ELECTROPORATION BASED DRUG DELIVERY SYSTEM, METHODS FOR USE AND FABRICATION THEREOF

TECHNICAL FIELD

The present invention relates to a drug delivery system and method for using thereof based on micro-electroporation, and also a method of fabricating the same.

BACKGROUND

Harnessing immune response to target and eradicate tumor cells, immunotherapy represents a transformation for cancer treatment aside from conventional radiotherapy and chemotherapy, including the use of antibodies (e.g., anti-PD-1), immune cells (e.g., dendritic cells), and genes (e.g., DNA) to boost immune response. Among the various types of cancer immunotherapy manners, DNA vaccination has emerged as the most promising alternative due to its high capability to induce tumor-specific immune responses. Before that, an essential requirement for DNA vaccination is that the DNA vaccines should pleasantly enter the host cells to express encoded antigens and to be processed by the antigen-presenting cells (APCs, such as Langerhans cells and dendritic cells) eventually. However, the efficacy of cancer immunotherapy using DNA vaccines remains unsatisfactory, partially due to insufficient antigens transportation to APCs and low efficacy to recruit and activate APCs. In this regard, it is important to develop an efficient gene transfection method to promote the cytosolic delivery efficacy of tumor-specific DNA vaccines and induce a robust immune response.

Currently, the most widely used technique for the delivery of DNA vaccines is intramuscular (IM) injection. However, naked DNA injection typically yields low transfection efficiency. To tackle this problem, several approaches such as cationic lipids/polymer encapsulation, electroporation, particle-assisted delivery, and pressurized delivery of micro-droplets have been developed to enhance transfection efficiency, among which electroporation is deemed as the most convenient method. In a typical example, Brave et al. (2011) reported that the DNA vaccination induced by skin electroporation succeeded in promoting $CD4^+$ and $CD8^+$ T cell responses, IFN-γ levels, and humoral immune responses. Despite the promise, generally, the gene should be injected into the corresponding tissue in liquid formulations before electroporation, hindering gene delivery in a controlled and precise way. From a technical perspective, liquid formulations inevitably raise the cost of storage and transportation, because DNA or RNA vaccines should be preserved at extremely low temperatures to keep their bioactivity. For instance, the administration of mRNA vaccine relies on LNPs, which has been proved to have several drawbacks and side effects, including technical barriers of encapsulating mRNA with LNPs, higher cost, allergic reactions caused by LNPs, and "cold chain" needed for transportation and storage, etc. In addition, conventional electroporation using high voltage (>200 V) usually results in a high level of cell death and a strong sense of pain, presenting a major obstacle for clinical translation.

In recent years, microneedle techniques have been developed as advanced drug intracellular delivery platforms to carry and administer therapeutic agents in a minimally invasive manner. Since the human epidermis is enriched with immune cells, skin plays an essential role in taking up antigens and executing immune surveillance. As a result, skin is a particularly attractive delivery target for genetic immunotherapy. However, the traditional transdermal microneedles can only carry a trace amount of DNA (e.g., plasmid) to the skin without the assistance of extra cationic microprotrusions, leading to rapid DNA clearance and low immunogenicity efficiency.

A need therefore exists for an electrically conductive microneedle platform serving as both electrodes and microprotrusions of nucleic acid molecules whilst inducing in situ intracellular electroporation and cytosolic nucleic acid delivery in a less invasive, painless, inexpensive, safe, highly efficient, and clinically feasible way such as in a form of a skin patch.

SUMMARY OF THE INVENTION

Accordingly, a first aspect of the present invention provides an electrically conductive and electricity-driven drug delivery system. The drug delivery system includes the following key components:

- an electrically conductive drug delivery device including an array of microprotrusions (e.g., microneedles) where each of the microprotrusions contains substances or molecules to be delivered to a target site of a recipient when a tip portion of each of the microprotrusions contacts a surface of the target site of the recipient under an electrical stimulation; and
- an electric circuit connected with the electrically conductive drug delivery device to provide electric current to the array of the microprotrusions in order to electrically induce a transcutaneous administration of the substances or molecules to the target site of the recipient,
- where the electrically conductive drug delivery device, after being electrically connected to the electric circuit, serves as an electrode of the electric circuit and induces an electro-osmosis to trigger a release of the substances or molecules from the tip section of the microprotrusion to the target site of the recipient in the absence of any assistive mechanical or actuation means;
- the electric circuit is configured to provide an electric current sufficient for the electrically conductive drug delivery device to induce the transcutaneous administration of the substances or molecules to the target site of the recipient without affecting physical and chemical properties of the substance or molecules, nor inducing specific immune response by the recipient to the contact between the tip section of the microprotrusions and the surface of the target site.

In certain embodiments, the primary target site of the present system is skin of the recipient. The present system is possible to be used in other target sites including, but not limited to, oral mucous membrane, gastrointestinal mucosa membrane, and external or internal mucosa membrane of organs. The present system is also applicable to natural or synthetic membranes for delivery of substances or molecules in vitro, ex vivo and in vivo.

In certain embodiments, the synthetic membranes include any chemically-formed membrane-like structures with or without cultured cells. For example, the synthetic membranes may be derived from GelMA, gelatin, chitosan, or any combination thereof, with or without cell cultures.

In certain embodiments, the target site includes 3D cultured cell hydrogel bulk.

In certain embodiments, the 3D cultured cell hydrogel bulk includes one or more of gelatin-based hydrogel, alginate-based hydrogel, chitosan-based hydrogel, and PEG-based hydrogel.

In certain embodiments, the array of microprotrusions includes a microporous structure derived from a hydrogel component, where the microporous structure has an average pore size of about 1 nm to 200 μm.

In certain embodiments, the hydrogel component includes one or more polymers which is/are biocompatible and biodegradable. More specifically, the one or more polymers are one or more of poly (lactic-co-glycolic acid) (PLGA), poly (glycolic acid) (PGA), poly-L-lactide (PLA), polyvinyl alcohol (PVA), polyvinylpyrrolidone (PVP).

In certain embodiments, the hydrogel components are in a concentration of about 0.1 wt. % to 60 wt. % in the array of microprotrusions.

In certain embodiments, the array of microprotrusions further includes an electrically conductive component.

In certain embodiments, the electrically conductive component includes one or more conductive materials of PEDOT:PSS, polythiophene (PTh), carbon nano tube, polypyrrole (PPy), polyaniline, and Mxene.

In certain embodiments, the electrically conductive component is in a concentration of about 0.1 wt. % to 90 wt. % in the array of microprotrusions.

In certain embodiments, the substances or molecules to be delivered by the present system includes nucleic acid-based vaccines and biomacromolecules in the absence of carrier which is normally required for other conventional administration routes such as intramuscular, intraturmoal and intranodal injections.

In certain embodiments, the biomacromolecules include proteins and peptides, or any fragment thereof.

In certain embodiments, the nucleic acid-based vaccines can be DNA and RNA vaccines, and the RNA vaccines can be linear or circular mRNA vaccines or both, and the DNA vaccines can be DNA plasmids capable of expressing one or more antigenic proteins in the recipient.

In certain embodiments, the nucleic acid-based vaccines are loaded into each of the microprotrusions at a weight of about 1 pg to 100 g.

In certain embodiments, the electric circuit includes a negative electrode, a connection between the negative electrode and the electrically conductive drug delivery device, and a power supply.

In certain embodiments, the connection can be a pair of magnetic clips for securing the electrically conductive drug delivery device to the negative electrode.

In certain embodiments, the negative electrode includes one or more conductive materials of copper, silver, iron, tin and aluminum.

In certain embodiments, the power supply connects to the negative electrode and the electrically conductive drug delivery device, respectively, to provide an electric current from 1 nA to 500 A, or a voltage from 1 nV to 500 V, or a pulse voltage from about 1 mV to 200 V at a pulse duration from about 1 ms to 10 s.

In other embodiments, the present system further includes a supporting medium for the array of the microprotrusions, for example, a pedestal.

In certain embodiments, the pedestal is made of the same material as that of the array of microprotrusions.

In other embodiments, the pedestal is made of a different material from that of the array of microprotrusions.

In the embodiments that the pedestal is made of the same material as that of the array of microprotrusions, the substances or molecules to be delivered can also be added in the pedestal.

In the embodiments that the pedestal is made of a different material from that of the array of microprotrusions, the pedestal can be made of one or more materials including, but not limited to, metal, glass, stone, and diamond.

In certain embodiments, the electrically conductive drug delivery device can be a patch used on a skin surface of the recipient with or without an adhesive layer for securing the patch on said skin surface.

In a second aspect, the present invention provides a method for delivering substances or molecules to a target site of a subject based on micro-electroporation and electro-osmosis, where the method includes:

- providing the electrically conductive and electricity-driven drug delivery system described in the first aspect or hereinafter in certain embodiments or examples;
- contacting a tip section of an array of microprotrusions with a surface of the target site of the subject;
- electrically activating the electrically conductive and electricity-driven drug delivery system by an electric stimulation to the electrically conductive drug delivery device through the electric circuit in order to initiate the micro-electroporation;
- triggering release of the substances or molecules from the tip section of the array of microprotrusions by the electro-osmosis to the target site through a reduction of conductive component of the microprotrusions when the electrically conductive and electricity-driven drug delivery system is electrically activated.

In certain embodiments, the electric stimulation to the electrically conductive drug delivery device through the electric circuit is by supplying a constant electric current or voltage, or a pulse voltage.

In certain embodiments, the constant electric current can be in a range from about 1 nA to 500 A; the constant voltage from about 1 nV to 500 V; the pulse voltage can be in a range from about 1 mV to 200 V at a pulse duration from about 1 ms to 10 s.

In certain embodiments, the target site of the subject comprises skin, oral mucous membrane, gastrointestinal mucosa membrane, and external or internal mucosa membrane of organs, and wherein the subject comprises mouse, rat, pig, rabbit, frog, cattle, horse, non-human primate animals such as rhesus monkey and Cynomolgus Monkey, etc., and human.

In certain embodiments, the target site of the subject includes skin, oral mucous membrane, gastrointestinal mucosa membrane, and external or internal mucosa membrane of organs.

In certain embodiments, the target site may also include natural or synthetic membranes for delivery of substances or molecules in vitro, ex vivo and in vivo.

In certain embodiments, the synthetic membranes include any chemically-formed membrane-like structures with or without cultured cells. For example, the synthetic membranes may be derived from GelMA, gelatin, chitosan, or any combination thereof, with or without cell cultures.

In certain embodiments, the target site includes 3D cultured cell hydrogel bulk.

In certain embodiments, the 3D cultured cell hydrogel bulk includes one or more of gelatin-based hydrogel, alginate-based hydrogel, chitosan-based hydrogel, and PEG-based hydrogel.

In a third aspect, the present invention provides a method for fabricating the electrically conductive and electricity-driven drug delivery system described in the first aspect or hereinafter in other embodiments or examples, comprising:

- preparing a hydrogel-based conductive polymer composition for forming the electrically conductive drug delivery device;

providing a mold with multiple cavities corresponding to shape and dimension of the microprotrusions of the electrically conductive drug delivery device;

casting the hydrogel-based conductive polymer composition into the mold until the hydrogel-based conductive polymer composition is set to form the array of microprotrusions;

demolding the array of microprotrusions from the mold and securing thereof to a negative electrode of the electric circuit.

In certain embodiments, the preparation of the hydrogel-based conductive polymer composition includes: mixing a hydrogel component with a conductive component to form a precursor solution; and adding the substances or molecules into the precursor solution, where the hydrogel component includes one or more biocompatible and biodegradable polymers of poly (lactic-co-glycolic acid) (PLGA), poly (glycolic acid) (PGA), poly-L-lactide (PLA), polyvinyl alcohol (PVA), polyvinylpyrrolidone (PVP) in a concentration of about 0.1 wt. % to 60 wt. %; and the conductive component includes one or more of PEDOT:PSS, polythiophene (PTh), carbon nano tube, polypyrrole (PPy), polyaniline, and Mxene in a concentration of about 0.1 wt. % to 90 wt. %.

In certain embodiments, the hydrogel component is PVA while the conductive component is PEDOT:PSS.

In certain embodiments, about 0.3 wt. % of the PEDOT:PSS is mixed with about 15 wt. % of PVA to form a composition for subsequent casting in the mold to form the array of microprotrusions.

In certain embodiments, solvent used to dissolve the biodegradable and biocompatible polymers includes water, phosphate buffer solution, alcohol, and physiological salt solution.

In certain embodiments, the polymers are FDA-approved, or NMPA-approved, or EMA-approved.

In certain embodiments, the substances or molecules include nucleic acid-based vaccines and biomacromolecules which are carrier-free.

In certain embodiments, the biomacromolecules include proteins and peptides, or any fragment thereof.

In certain embodiments, the nucleic acid-based vaccines are DNA or RNA vaccines added at a weight of about 1 pg to 100 g per microprotrusion into the composition prior to casting in the mold.

In certain embodiments, the mold has multiple cavities each in a dimension complementary to the dimension of each of the microprotrusions after casting the composition.

In certain embodiments, each of the microprotrusions has an average length of about 950 μm, an average base diameter of 380 μm, and the array has a gap distance of about 320 μm among two adjacent microprotrusions.

In certain embodiments, the as-fabricated array of microprotrusions includes a microporous structure with an average pore size of about 1 nm to 200 μm.

In other embodiments, the as-fabricated array of microprotrusions may have an average conductivity of about 1.2 to 2.7 S/m and an average failure force of about 0.4 N per microprotrusion.

Other aspects of the present invention includes a method for vaccinating a subject with a nucleic acid-based vaccine including using the present drug delivery system to transcutaneously administer the nucleic acid-based vaccine to the subject, and the vaccine may include, but not limited to, COVID-19, HIV, cancer, tetanus, anthrax, influenza, rabies, rotavirus, diphtheria, hepatitis A, yellow fever, hepatitis B, polio, rubella, pneumococcal diseases, pertussis, Haemophilus influenza type b, varicella, human papillomavirus, Japanese encephalitis, Lyme disease, measles, meningococcal and mumps, shingles, smallpox, tuberculosis, typhoid vaccines.

The present drug delivery system can also be fabricated into other forms including blade, pad, sheet, bulk, and cylinder, than just the patch for transdermal application described herein, subject to the target site of administration and/or the substances or molecules to be delivered.

The present drug delivery system is also applicable in different therapeutic regime including gene therapy, cancer therapy, immunotherapy, and different vaccination schemes.

The present drug delivery system is also useful in basic and medical researches, preclinical and clinical trial studies, and also in clinical applications. Due to the ease of storage, transportation, application, and low safety measures required in the present invention compared to conventional injection methods which involve more invasive means of administration and require proper training before administration, the present system is also more suitable for personal use with minimal training and less supervision.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Other aspects of the present invention are disclosed as illustrated by the embodiments hereinafter.

BRIEF DESCRIPTION OF DRAWINGS

The patent or application file contains at least one drawing executed in color. Copies of this patent or patent application publication with color drawing(s) will be provided by the Office upon request and payment of the necessary fee.

The appended drawings, where like reference numerals refer to identical or functionally similar elements, contain figures of certain embodiments to further illustrate and clarify the above and other aspects, advantages and features of the present invention. It will be appreciated that these drawings depict embodiments of the invention and are not intended to limit its scope. The invention will be described and explained with additional specificity and detail through the use of the accompanying drawings in which.

Skilled artisans will appreciate that elements in the figures are illustrated for simplicity and clarity and have not necessarily been depicted to scale.

DETAILED DESCRIPTION OF THE INVENTION

It will be apparent to those skilled in the art that modifications, including additions and/or substitutions, may be made without departing from the scope and spirit of the invention. Specific details may be omitted so as not to obscure the invention; however, the disclosure is written to enable one skilled in the art to practice the teachings herein without undue experimentation.

The present disclosure provides a potential delivery system based on a plurality of conductive hydrogel microelectrodes (CHME) for transdermal delivery of different substances or molecules including, but not limited to, one or more nucleic acids in any conformation, including DNA, RNA, or both, single-stranded or double-stranded, or any fragment, variants, microprotrusions, vectors, recombinants, combination thereof with other substance or molecule than DNA or RNA.

Therefore, the delivery system based on the CHME in certain embodiments can be used for gene therapy and immunotherapy for a wide variety of diseases or conditions devoid of other unknown immune response induced by conventional administration method such as through intramuscular, intravenous, intratumoral, or other more invasive methods than the present system through a minimal contact by a plurality of microneedles on a subject's skin.

Figure 1A:
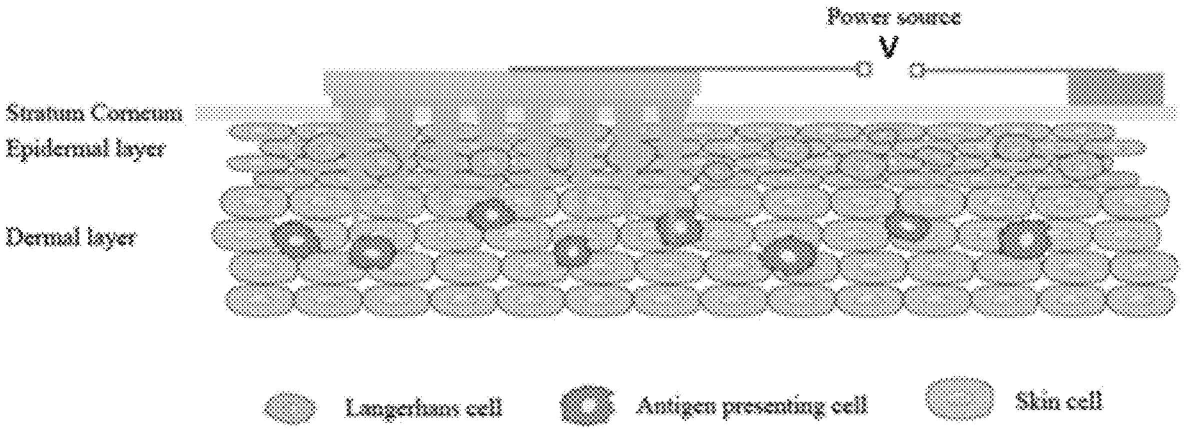
FIG. 1A schematically depicts the working principle of the transdermal drug delivery system according to certain embodiments of the present invention.

FIG. 1 illustrates generally the working principle of the present transdermal delivery system on a human skin area in terms of the application in an electroporation-mediated cancer immunotherapy. The present transdermal drug delivery system can be generally divided into two parts. A first part is an array of microneedles secured on a substrate as an interface to contact with an area on human skin and deliver an intended substance or molecule to a target site where a corresponding response will be triggered by the substance or molecule delivered thereto, instead of the puncture action by the interface of the delivery system with the human skin. A second part of the present transdermal drug delivery system is an electric circuit connecting to the conductive part of the transdermal interface of the present delivery system, i.e., the array of microneedles, or more specifically, the CHME. The microneedles according to certain embodiments of the present invention serve as both flexible electrodes and containers of the intended substance or molecule to be delivered, which can achieve a controlled release of the intended substance or molecule from an encapsulation form under an electricity-driven mechanism with an aid of a pulse generator to realize an efficient micro-electroporation in vivo. In certain embodiments, applying the present system for providing a cancer immunotherapy in a small animal model such as mouse model can induce a robust immune response by delivering a relatively low dose of DNA plasmid, e.g., 10 μg, which is about one-tenth of the dose administered by intramuscular (IM) injection (i.e., 100 μg of plasmid) in a single dosing, to achieve a comparable immune response. In some examples described herein, it is further demonstrated that the present system is a promising platform to elicit striking anti-tumor T-cell responses and in turn inhibiting tumor growth. The present invention is facile in preparation, self-administrable, robust in prophylactic and therapeutic effects, rendering a multi-functional delivery platform for a wide range of materials from cancer therapeutics, vaccines, to other bioactive substances or molecules.

In some other examples provided in this section, safety, biocompatibility, and cell viability of using the present system to deliver the intended substance or molecule to various in vivo model based on micro-electroporation will be verified.

Fabrication and Characterization of Conductive Hydrogel Micro-Electroporation (CHME) Platform As described herein, the CHME platform includes a plurality of electrically conductive microneedles each encapsulating the substance or molecule to be delivered to a target site of a host upon electric stimulation to the microneedles in order to enable a micro-electroporation of the substance or molecule to the target site.

Turning to FIG. 2A-2L, a prototype of the array of electrically conductive microneedles is provided (FIG. 2A) and mounted on an adhesive tape (FIG. 2B) to secure the attachment of the CHME on the target site of the host, e.g., on the skin of an upper arm of a human (FIG. 2C), and the intended substance or molecule to be delivered in this example is a nucleic acid vaccine such as DNA or RNA vaccine being encapsulated in each of the microneedles.

Figure 2A:
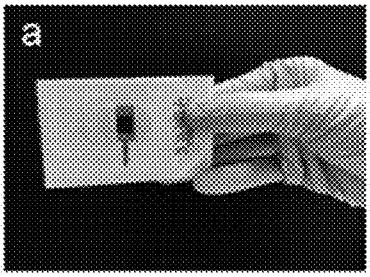
FIG. 2A shows an image of an array of microneedles of the transdermal drug delivery system according to certain embodiments of the present invention.
Figure 2B:
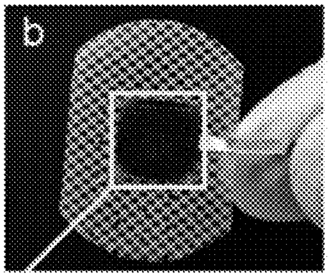
FIG. 2B shows an image of the array of microneedles as shown in FIG. 2A secured on an adhesive tape to form a patch.
Figure 2C:
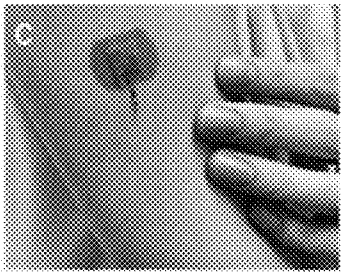
FIG. 2C shows an image of applying the patch as shown in FIG. 2B on skin around wrist section of a subject.
Figure 2D:
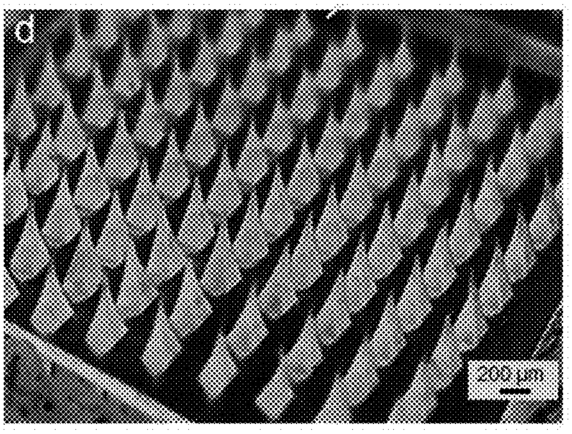
FIG. 2D is an image showing from a perspective view an array of microneedles of the transdermal drug delivery system according to certain embodiments of the present invention; scale bar: 200 μm.
Figure 2E:
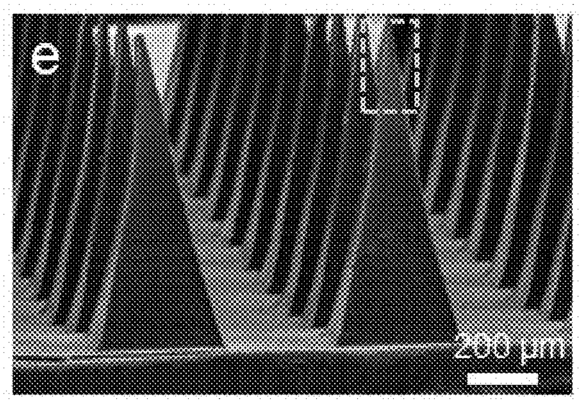
FIG. 2E is an SEM image showing from a lateral view the array of the microneedles as shown in FIG. 2D; scale bar: 200 μm.
Figure 2F:
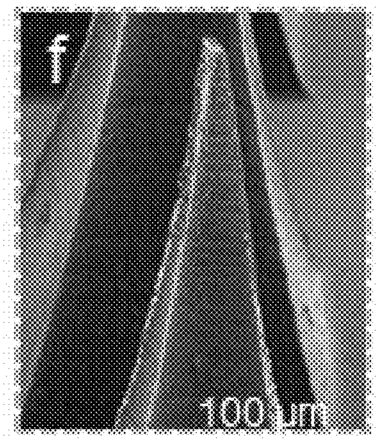
FIG. 2F is an SEM image showing from an oblique view the array of the microneedles as shown in FIG. 2D; scale bar: 100 μm.

In certain embodiments, the method of preparing the CHME encapsulating a DNA vaccine includes: mixing an electrically conductive component, e.g., PEDOT:PSS dispersion (0.3 wt %), with polyvinyl alcohol (PVA) to form a precursor solution, where PVA is chosen as a patch matrix because of its unique characteristics including cross-linking structure, non-toxicity, good biocompatibility and swelling ability; adding the intended DNA vaccines to the precursor solution subsequently; casting the mixture in a mold to form the array of microneedles in a patch form under an air-drying condition. This preparation method avoids the need for organic solvents and elevated temperatures which may potentially affect biomolecule stability of DNA vaccines or even damage them. The single-step casting molding allows a high throughput loading with high consistency and efficiency. A perspective view image of the as-prepared microneedles in FIG. 2D shows that substantially uniform pyramid shaped microneedles are evenly spaced apart from each other and arranged in a 10×10 array format in this example. The number, spatial distribution, shape and dimension of the microneedles can be tuned by selecting a suitable mold to cast the intended substance or molecule containing hydrogel solution. Lateral and oblique views focusing on the tip of the microneedles in SEM images of FIGS. 2E and 2F, respectively, confirm the uniformity, spatial distribution, shape and dimension of the microneedles formed by this single-step casting molding from the hydrogel formulation provided in this example, in which the microneedles have an average length of about 950 μm, average base diameter of 380 μm, and average gap distance of about 320 μm between the adjacent two microneedles.

Figure 2G:
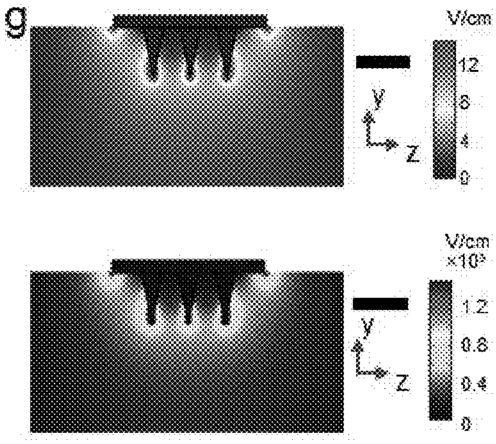
FIG. 2G shows a simulated electric field distribution of the transdermal drug delivery system according to certain embodiments of the present invention under 1V (upper panel) or 90V (lower panel); scale bar: 1 mm.
Figure 2H:
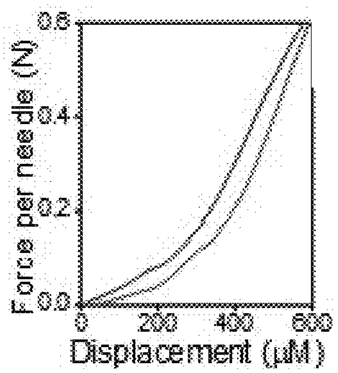
FIG. 2H shows the change in mechanical force of the microneedles of the present system according to certain embodiments against displacement between the microneedles and the skin of the subject.
Figure 2I:
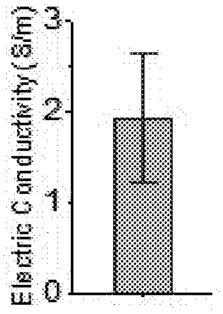
FIG. 2I shows the electric conductivity of the present system according to certain embodiments.
Figure 2J:
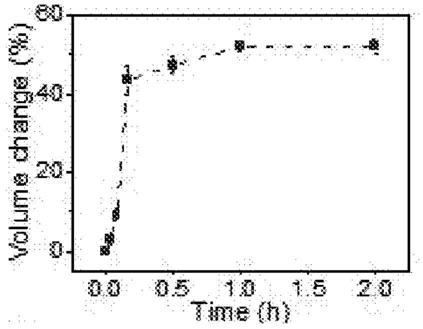
FIG. 2J shows the swelling behavior of the present system in agarose gel according to certain embodiments.
Figure 2K:
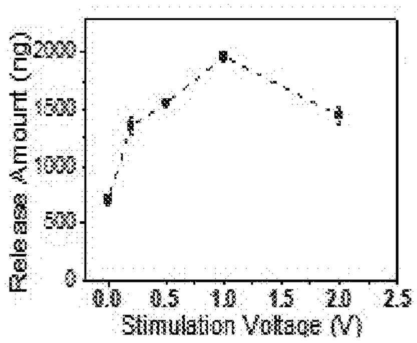
FIG. 2K shows the release amount of substance to a target site by the present system against different levels of external electric stimulation.
Figure 2L:
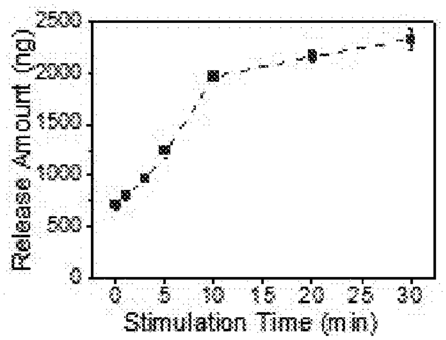
FIG. 2L shows the release amount of substance to a target site by the present system against different time durations of external electric stimulation.
Figure 2M:
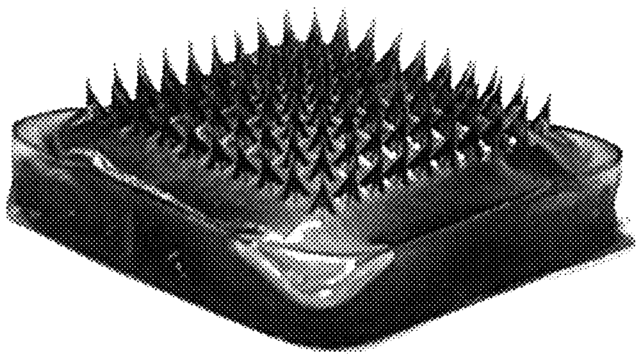
FIG. 2M schematically depicts the present system with a support medium according to certain embodiments of the present invention.
Figure 2N:
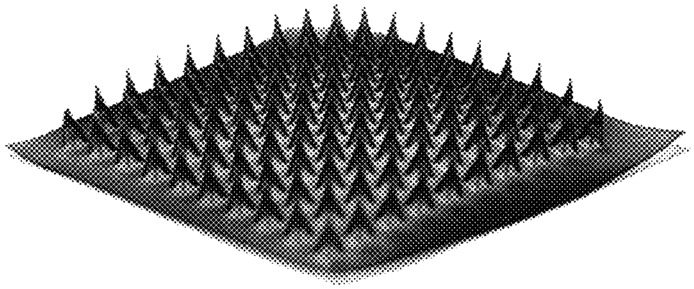
FIG. 2N schematically depicts the present system without a support medium according to certain embodiments of the present invention.

In certain embodiments, the array of microneedles is further supported by a pedestal (FIG. 2M). In other embodiments, the array of microneedles can be used without a support medium, e.g., no pedestal. (FIG. 2N), depending on the application.

Figure 1B:
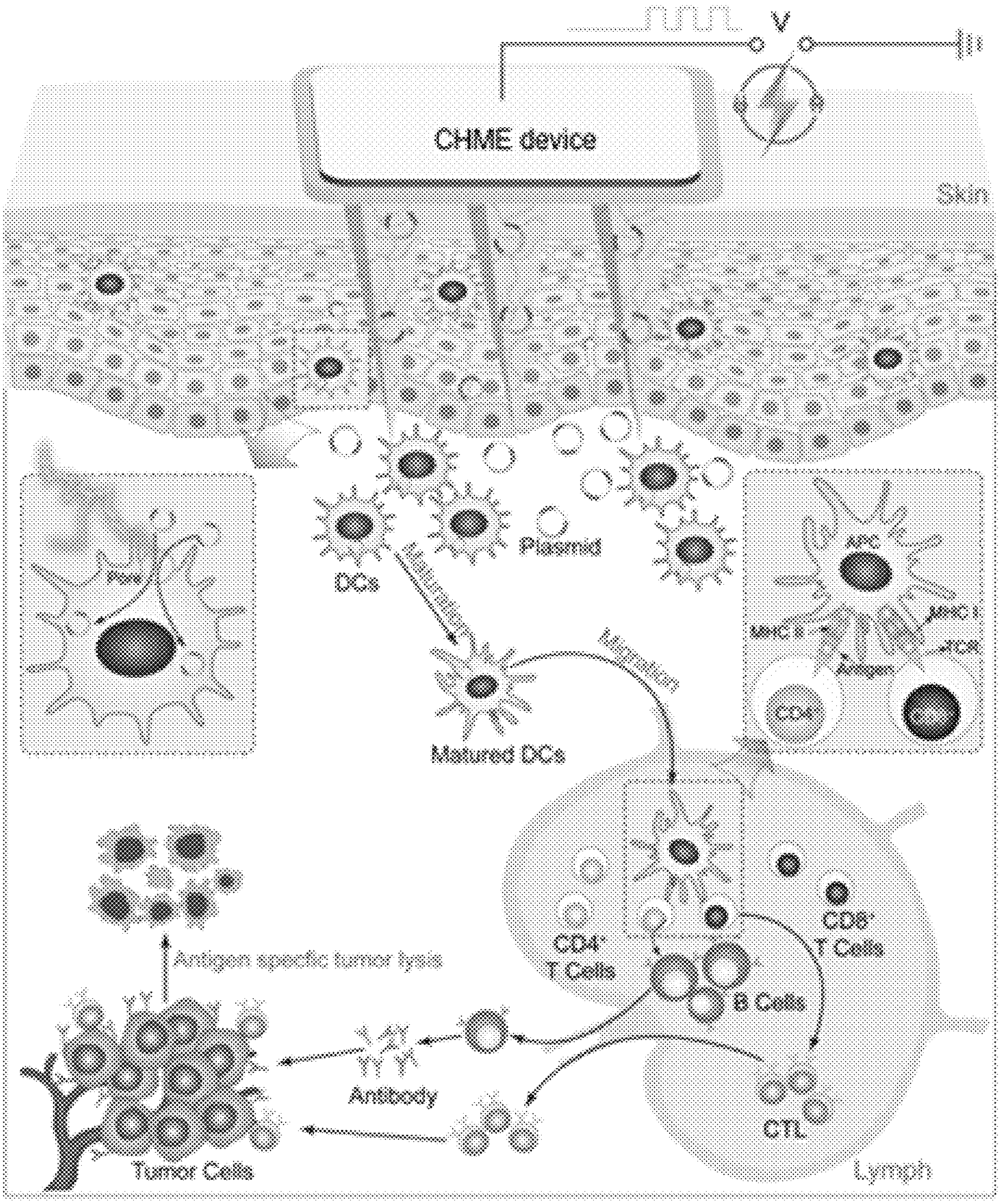
FIG. 1B schematically depicts physiological and immunological changes in different skin layers upon electric stimulation of the transdermal delivery system when contacting the skin surface according to certain embodiments of the present invention.

Since the CHME integrates loading, release (by electro-osmosis) and transfection (by electroporation) of nucleic acids into a single operation to induce a robust immune response required for effective protection, it is better to study electric field distribution of the microneedles across the whole array. One of the parameters affecting the electric field distribution is the electric field strength. FIG. 2G shows that the highest electric field is measured at the tip of the microneedles, where electrode curvature is known to enhance the electric field strength. It is known that the threshold value for reversible in vivo electroporation depends on both the voltage and duration of electrical pulses. For millisecond pulses, the electroporation threshold is expected to be in an order of 400-600 V/cm. When a 90 V pulsed voltage is used, it is found that the electric field does not penetrate deeply into the tissue below the electrodes, as it drops off on a length scale of hundreds of microns. In this way, the electric field is beyond the threshold at the epidermis and upper layer of the dermis, where abundant antigen-presenting cells, such as Langerhans cells and dendritic cells, are contained (FIG. 1B). Thus, the effective release of DNA vaccines and in vivo electroporation are realized using such an electric stimulus, and the physical pain induced by high-voltage injury can be avoided at the same time.

To test the structural stability, thermogravimetric analysis (TG) is conducted on the CHME platform. The TG curves of PVA microneedles with and without PEDOT:PSS show that the inclusion of PEDOT:PSS improves the total stability because the degradation temperature of the polymer structure increase greatly from the 260° C. to 423° C.

Turning to FIG. 2H, the mechanical properties of the CHME platform is also evaluated to validate the performance of skin penetration. The average failure force of the microneedles is measured to be 0.4 N/needle, which is sufficient to facilitate insertion into the skin without structural breaking.

Turning to FIG. 2I, the electrical test indicates that the hydrogel-based microneedles show an excellent conductivity of 1.93±0.71 S/m. The excellent mechanical and electrical performances make the CHME platform suitable for in vivo application. The swelling abilities of the present cross-linked CHME platform are also tested by measuring the volume change before and after its incubation in agarose hydrogels (1.5% w/w in PBS), mimicking the swelling abilities in vivo. The result in FIG. 2J shows that the swelling ratios of the CHME device reach a plateau after incubation for about 10 minutes. The fast swelling is beneficial to a further electricity-driven release of biomacromolecules.

Electricity-Driven Release of Biomacromolecules by the CHME Platform

Turning to FIGS. 2K and 2L, an ovalbumin (OVA) plasmid as a nucleic acid vaccine model is encapsulated into the hydrogel microneedles and the CHME platform is inserted into an agarose hydrogel (1.5% w/w in PBS) to study the electricity-driven release kinetics of the CHME platform. The agarose hydrogel is used as a biomimetic substrate to mimic the skin environment. In the electricity-driven release process, the negatively charged OVA plasmid can be extracted from the microneedles to enter agarose hydrogel, owing to the electro-osmosis induced by a negative electric potential. As a result, the released number of plasmids in agarose hydrogel is used to quantitatively analyze the releasing performance. The release is associated with the electric voltage and electric stimulation duration. For example, at a fixed pulse duration of 10 minutes, the release amount reaches the maximum when a voltage of 1.0 V is applied. Too low voltage will cause insufficient release, whereas too high voltage will cause bioactivity loss. Thus, a fixed 1 V electricity is selected to study the optimal stimulation duration. It is found that the release amount reaches a plateau for about 10 minutes, with a plasmid release amount of 1964±40 ng. It should be noted that the release amount from the CHME platform under an electrically driven condition can be three-folds higher than that from a passive diffusion, demonstrating its effectiveness. In addition, effective releasing kinetics is also observed for other plasmid such as eGFP plasmid.

Figure 3A:
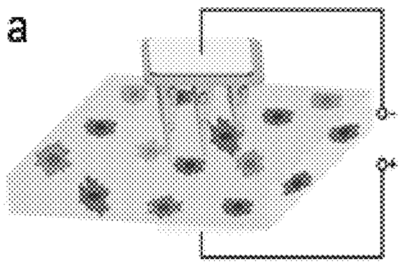
FIG. 3A schematically depicts a setup of an in vitro model to test the micro-electroporation performance of the present system according to certain embodiments.

In Vitro Cytotoxicity and Delivery Efficiency of Nucleic Acid Vaccine by CHME Platform Turning to FIGS. 3A-3H, intracellular delivery of the intended substance or molecule by the CHME platform is demonstrated on a commonly used ex vivo model, gelatin methacryloyl (GelMA)-based hydrogel, by preparing a 3D extracellular matrix encapsulating HEK293T cells to mimic skin tissue. As shown in FIG. 3A, cells are loaded into the GelMA hydrogel at where the CHME microneedles are inserted, then a negative voltage and pulse generator are applied to trigger release and electric pulse, respectively.

Figure 3B:
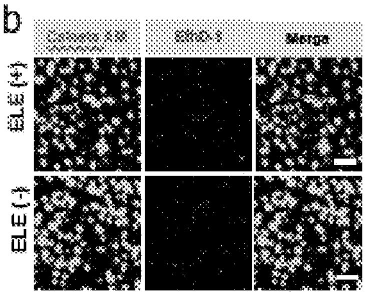
FIG. 3B shows a series of images for a cell viability test result after the micro-electroporation by the present system according to the setup as shown in FIG. 3A.
Figure 3C:
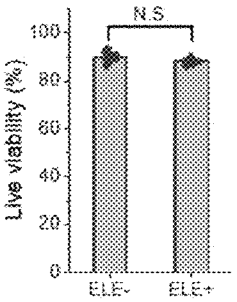
FIG. 3C shows quantitatively the cell viability test result of FIG. 3B; error bars indicate SEM, n=4; * indicates P<0.05; N.S.: not significant, by student-t test.

To demonstrate the safety of the release and electroporation process, a cell viability test is conducted one day after the electroporation operation. As shown in FIG. 3B, the cell viability around the micropores of the GelMA hydrogel having been inserted with the CHME microneedles reaches as high as 90%, which is close to that without electroporation (90.1±1.2%). Since no obvious cytotoxicity to cells is observed, it is suggested that the electricity-driven operation and in vivo electroporation process by the CHME platform are safe at least at an in vitro level.

Figure 3D:
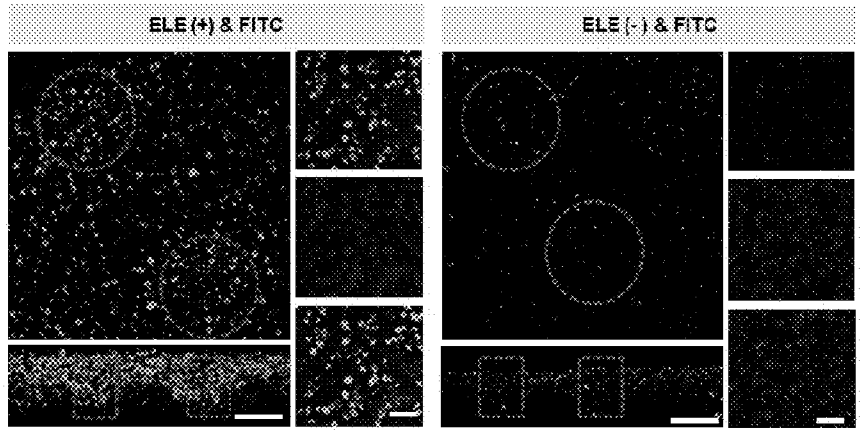
FIG. 3D shows 3D fluorescence images of a FITC-dextran transfection test of the present system with or without micro-electroporation in the in vitro model of FIG. 3A: from top view (top panel); from side view (bottom panel)
Figure 3E:
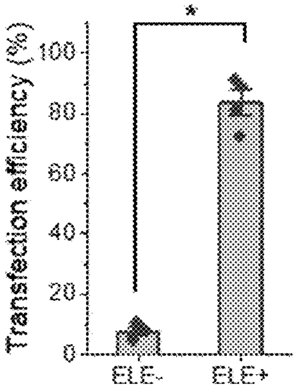
FIG. 3E shows quantitatively the transfection efficiency of the FITC-dextran after micro-electroporation by the present system according to the test as shown in FIG. 3D; error bars indicate SEM, n=4; * indicates P<0.05; N.S.: not significant, by student-t test.
Figure 3F:
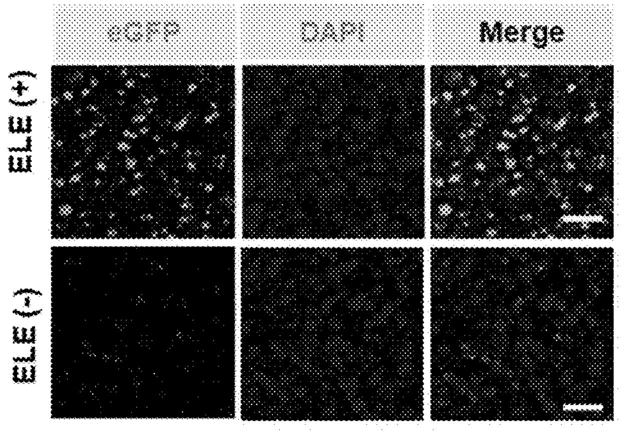
FIG. 3F shows fluorescence images of eGFP expression in the cells of the in vitro model of FIG. 3A delivered by the present system with micro-electroporation (top panel) and without micro-electroporation (bottom panel); scale bar: 100 inn.
Figure 3G:
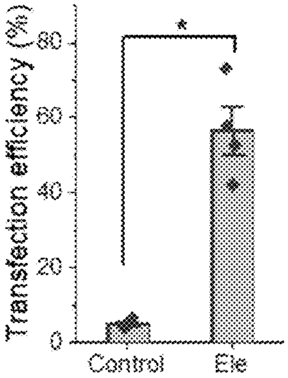
FIG. 3G shows quantitatively the eGFP expression of the cells as shown in FIG. 3F; error bars indicate SEM, n=4; * indicates P<0.05; N.S.: not significant, by student-t test.
Figure 3H:
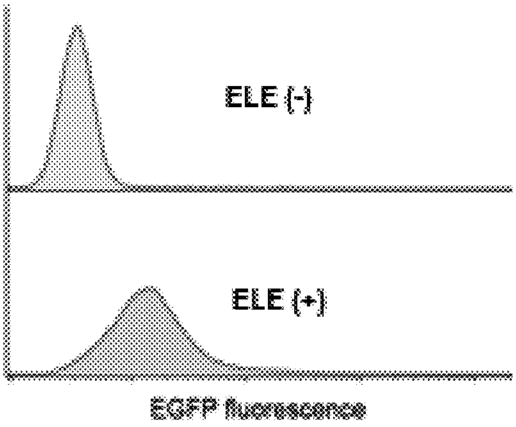
FIG. 3H shows a flow cytometry result of the eGFP expression in the cells with or without micro-electroporation delivered by the present system as in FIG. 3F.

To evaluate the effectiveness of macromolecules delivery into living cells, the HEK293T cells are initially transfected with 1 μg of FITC-dextran (3-5 kDa) per patch by the CHME platform. FIGS. 3D and 3E show that up to 80% transfection efficiency around microneedles at 90 V voltage (ELE (+) & FITC) is yielded, which is over 10-fold higher than that observed from a control group without electroporation operation (ELE (−) & FITC). The highly efficient delivery is further evidenced through 3D confocal imaging, which shows a prominent needle-shaped path in cell-laden hydrogels (FIG. 3D, bottom panels). After successful delivery of model macromolecules, the delivery of eGFP plasmid as a reporter gene to the HEK-293T-loaded hydrogel. The confocal microscopy images of FIG. 3F confirm the successful eGFP delivery after 24 hours when a 10 μg/patch of eGFP is used. Quantification of the confocal microscopy images in FIG. 3G reveals that up to 60% transfection efficiency at 90V, which further confirms quantitatively by flow cytometry (FIG. 3H). Taken together, these results show that the CHME platform can deliver large macromolecular complexes in vitro efficiently. Next, the delivery of macromolecules will be further studied in in vivo model.

In Vivo Gene Transfection by CHME Platform

Figure 4A:
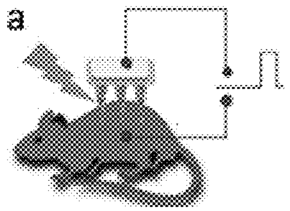
FIG. 4A schematically depicts the scheme of conducting biocompatibility test of gene transfection by the present system through micro-electroporation on an in vivo model according to certain embodiments of the present invention.
Figure 4B:
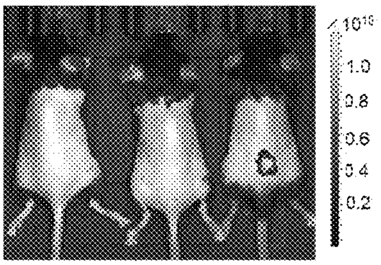
FIG. 4B shows fluorescence images on the in vivo model according to the scheme depicted in FIG. 4A right after micro-electroporation with a plasmid expressing a fluorescent protein delivered to the skin by the present system; from the left: control (without using the present system), with the present system but without applying electricity, with the present system and electricity applied.
Figure 4C:
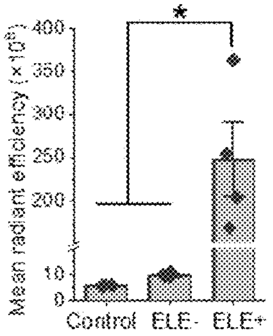
FIG. 4C shows quantitatively the fluorescence signals of the imaging result depicted in FIG. 4B; error bars indicate SEM, n=4, * indicates P<0.05, by student-t test.
Figure 4D:
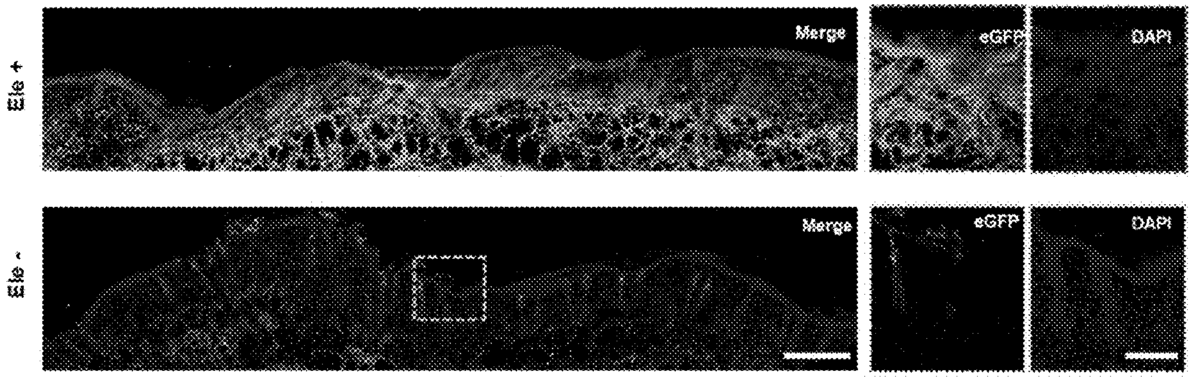
FIG. 4D shows fluorescence images on the in vivo model locally at where the plasmid is applied by the present system according to the scheme and test depicted in FIGS. 4A and 4B, respectively: with the present system and plasmid (top panel), with the present system (indicated by a broken lined box) but without the plasmid (bottom panel)
Figure 4E:
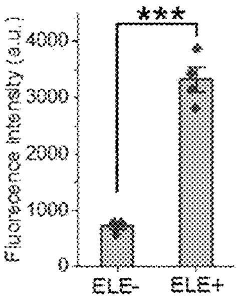
FIG. 4E shows quantitatively the fluorescence signals from the images depicted in FIG. 4D; error bars indicate SEM, n=4, * indicates P<0.05, by student-t test

Turning to FIGS. 4A-4G, gene transfection by the CHME platform is evaluated in a mouse model by inserting the CHME microneedles into its shaved skin through a thumb pressing process. A platinum electrode is used as a positive electrode, and a negative voltage is applied to the CHME microneedles to trigger the release of plasmid and in vivo electroporation (FIG. 4A). The delivery efficiency is initially assessed by taking FITC-dextran (3-5 kDa) as a model macromolecule. 30 minutes after delivery. A strong FITC fluorescence signal is found at the skin area of the mice where the CHME microneedles are inserted, under the in vivo system (FIG. 4B, right panel). In contrast, the FITC fluorescence signal is invisible for the control groups without applying the CHME device or without electricity treatment (FIGS. 4B and 4C). Subsequently, the successful delivery of FITC dextran at a penetrated site in the cellular level is confirmed by nuclear staining and FITC imaging. To evaluate the effects of the CHME platform on plasmid delivery and transfection, the electricity-driven process is performed to achieve both release and electroporation of eGFP plasmid. Quantified by the confocal imaging 24 h after electroporation, the CHME-treated group demonstrates a significantly improved eGFP expression, that is, three-fold higher fluorescence intensity in the penetration site, in contrast to the group without electroporation (FIGS. 4D and 4E).

Figure 4F:
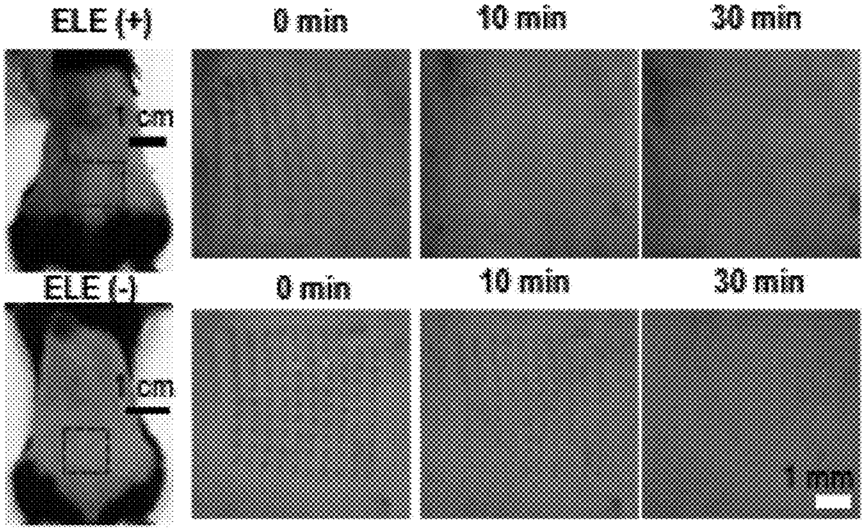
FIG. 4F shows images of the skin of the in vivo model with or without the micro-electroporation by the present system according to the scheme depicted in FIG. 4A and procedure depicted in FIG. 4B right after (0 min), 10 mins and 30 mins.
Figure 4G:
FIG. 4G shows images of histological section from the skin of the in vivo model with the micro-electroporation by the present system according to the scheme depicted in FIG. 4A and procedure depicted in FIG. 4B; scale bar in top panel=300 μm; bottom panel is a magnified image of the boxed area in the top panel with scale bar=100 μm.

To confirm the biocompatibility of the CHME platform, the mouse's skin is imaged immediately after electroporation. FIG. 4F shows that no obvious skin damage is observed at the administration site in both cases, with and without electroporation, and only microholes are observed on the skin immediately after administration as direct evidence of successful skin puncture. In addition, the microholes fade within 10 minutes and completely disappear after 30 minutes. Such a quick self-recovery testifies the safety of using electric stimulation in the CHME platform. Histological sectioning of skin treated with the CHME device show uniform patterns of microneedle insertion into the epidermis layer of the skin without disruption of underlying dermal layers of capillary vessels (FIG. 4G). Furthermore, histological examination of skin 24 h after administration by the CHME shows no inflammatory markers. The above data suggests the superior biocompatibility of the CHME platform without raising any safety concerns.

Evaluation of Immune Responses In Vivo Induced by CHME-Based DNA Vaccination

Figure 5A:
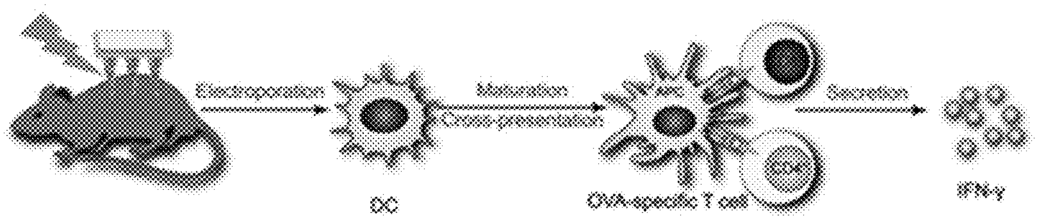
FIG. 5A schematically depicts the scheme of establishing an in vivo model to evaluate immune responses induced by the present system with a model antigen, ovalbumin (OVA), via micro-electroporation, and proposed mechanism of inducing the immune responses.
Figure 5B:
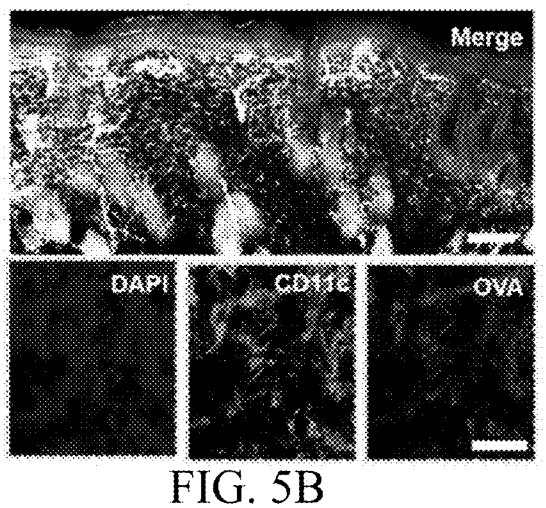
FIG. 5B shows fluorescence images for biomarkers of dendritic cells (DC, $CD11c^+$) and OVA-expressing cells (OVA+) in the skin of the in vivo model treated with micro-electroporation by the present system according to the scheme depicted in FIG. 5A.
Figure 5C:
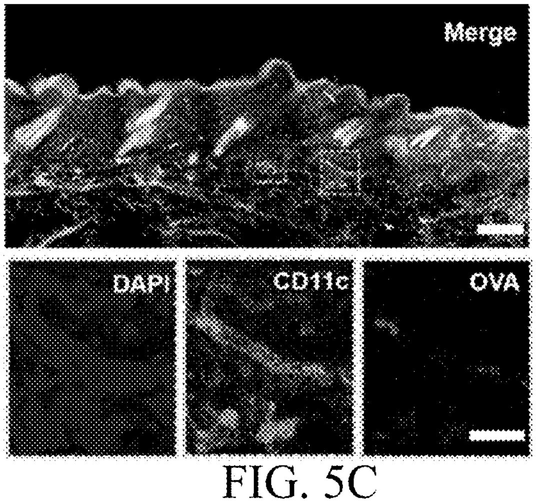
FIG. 5C shows fluorescence images for biomarkers of dendritic cells (DC, $CD11c^+$) and OVA-expressing cells (OVA+) in the skin of the in vivo model treated without micro-electroporation by the present system according to the scheme depicted in FIG. 5A.

Turning to FIGS. 5A-5I, to demonstrate that the CHME platform can significantly augment gene expression in vivo, the immunogenicity response using ovalbumin (OVA) as a model antigen with in vivo electroporation (labeled as OVA-ELE) and without electroporation (labeled as OVA), respectively, is evaluated on C57BL/6 mice (FIG. 5A). The treated skin is harvested 7 days after treatment for immunofluorescence imaging. The skin immunized with OVA-ELE significantly increases the number of recruited dendritic cells (DCs) ($CD11c^+$) and the fluorescence signal intensity of CD11c, compared to the control group with OVA only (FIGS. 5B and 5C). Furthermore, the co-localization of CD11c positive cells and OVA-expressing cells indicate the successful delivery of OVA to DCs, which is a crucial step to present antigen and initiate a subsequent antigen-specific immune response.

Figure 5D:
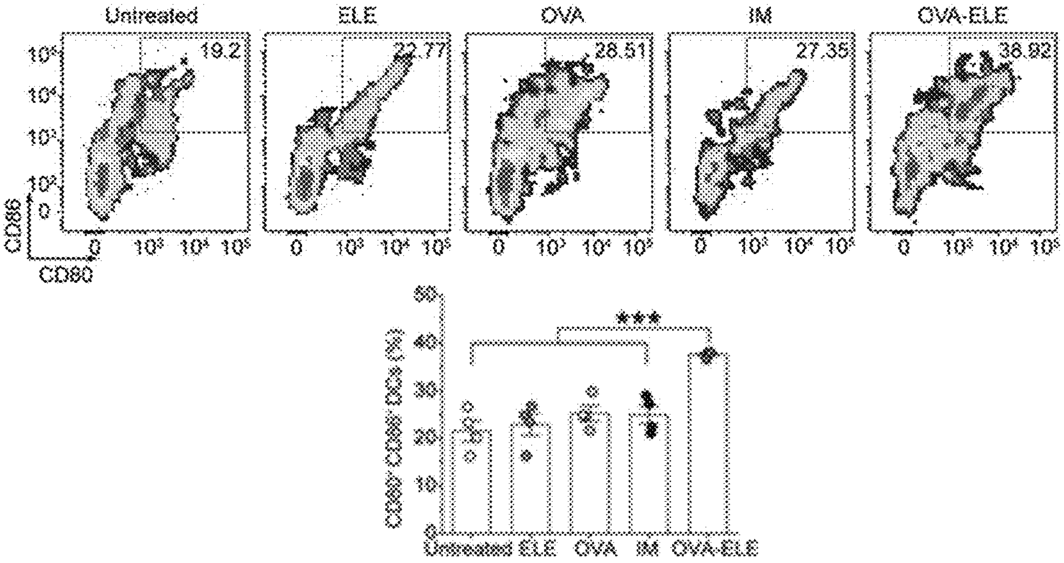
FIG. 5D shows flow cytometry result of a study on dendritic cell maturation in terms of different biomarker expressions from the draining lymph nodes (dLNs) of the in vivo model induced by different treatment groups (control; OVA-ELE; OVA; OVA-free ELE) on day 7 post-immunization by the present system, and a statistical representation of the biomarker expressions; ELE: micro-electroporation applied.
Figure 5E:
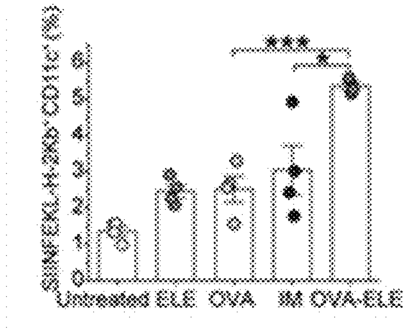
FIG. 5E shows cross-expression of $CD11c^+$SIINFEKL-H-$2Kb^+$ dendritic cells of dLNs from different treatment groups of the in vivo model treated by the present system according to the scheme depicted in FIG. 5A.
Figure 10A:
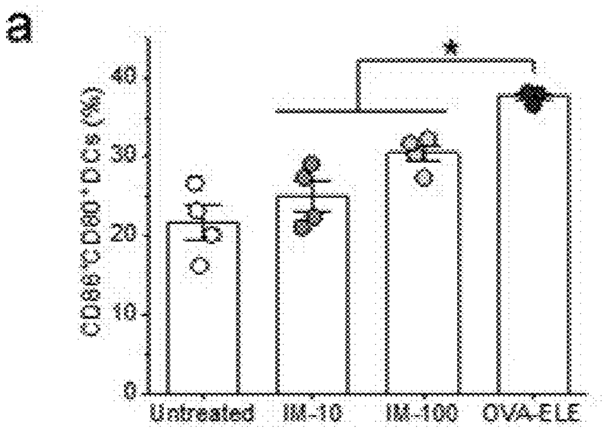
FIG. 10A shows the frequency of $CD80^{+}CD86^{+}$ among dLNs after the single vaccination under different conditions; IM-10: intramuscular administration of 10 μg plasmid; IM-100: intramuscular administration of 100 μg plasmid; OVA-ELE: using CHME platform with micro-electroporation (loaded with 10 μg plasmid); the data are presented as the mean±SEM; * indicates P<0.05 by student-t test.
Figure 10B:
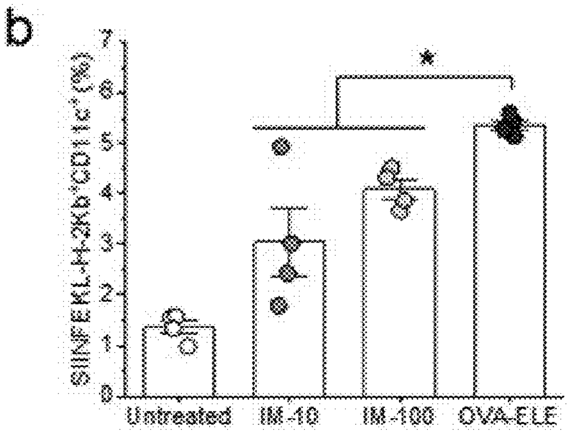
FIG. 10B shows the frequency of SIINFEKL-H-$2Kb^{+}$ $CD11c^{+}$ among dLNs after the single vaccination under different conditions; IM-10: intramuscular administration of 10 μg plasmid; IM-100: intramuscular administration of 100 μg plasmid; OVA-ELE: using CHME platform with micro-electroporation (loaded with 10 μg plasmid); the data are presented as the mean±SEM. * indicates P<0.05 by student-t test.

Next, the mice are immunized with the OVA-ELE (10 μg/patch), OVA (10 μg/patch), OVA-free ELE (labeled as ELE), intramuscular injection (labeled as IM) at two different doses (10 and 100 μg), and analyzed the draining lymph node (dLNs) 7 days after vaccination. Among different treatment groups, vaccination with the OVA-ELE induces an increased amount of CD80 and CD86 positive DCs (38.1±0.35%) in the dLNs (FIG. 5D). Notably, the OVA-ELE group also results in the highest level (5.37±0.1%) of $CD11c^+$SIINFEKL-H-$2Kb^+$antigen cross-presented DCs, compared to 1.36±0.13%, 2.46±0.18%, 2.52±0.36% and 3.04±0.68% for untreated, ELE, OVA and IM groups, respectively (FIG. 5E). Additionally, the mice immunized with OVA-ELE show significant enrichment of $CD11c^+$ $CD86^+$ and $CD11c^+CD80^+$activated DCs. Specifically, the OVA-ELE vaccination group could produce a higher level of DCs maturation and cross-presentation than IM vaccination group at both 10 μg and 100 μg doses (FIGS. 10A and 10B). The three times vaccination elicits a higher level of $CD11c^+$ $CD80^+CD86^+$DCs and $CD11c^+$SIINFEKL-H-$2Kb^+$antigen cross-presenting cells.

Figure 5F:
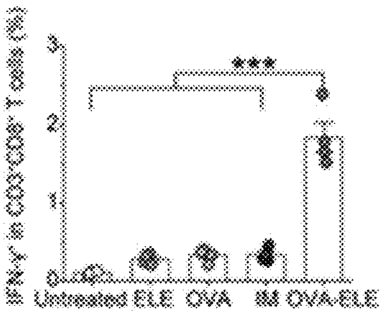
FIG. 5F shows the percentage of IFN-γ-positive cytotoxic T lymphocyte cells (CTLs) from circulating peripheral blood sample drawn on day 7 post-immunization from different treatment groups of the in vivo model treated by the present system according to the scheme depicted in FIG. 5A.
Figure 5G:
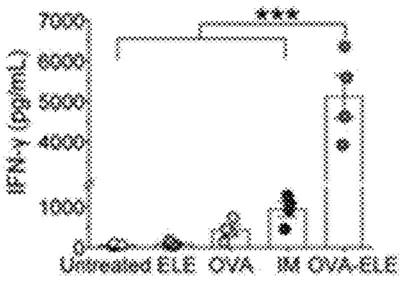
FIG. 5G shows IFN-γ secretion of splenocytes in the culture supernatants after restimulation of with OVA antigen for 72 hours in vivo model as shown in FIG. 5F.
Figure 5H:
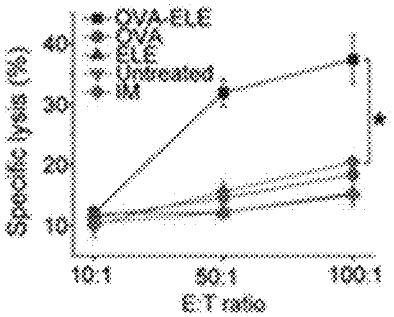
FIG. 5H shows the percentage of the lysis of target cells from samples of different treatment groups of in vivo model as in FIG. 5F.
Figure 5I:
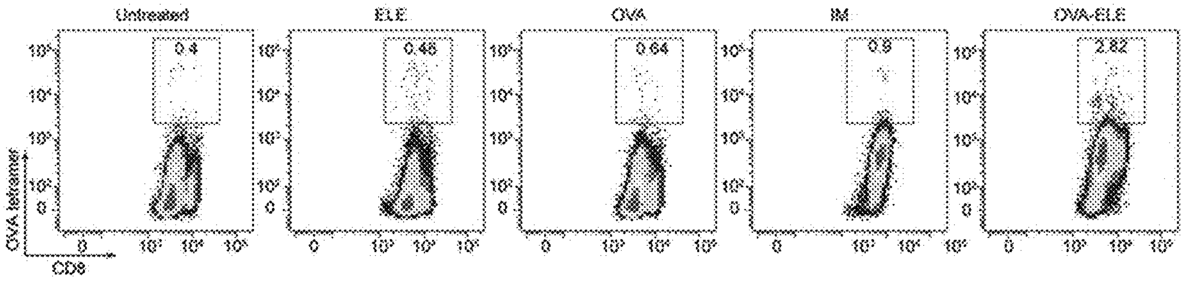
FIG. 5I shows flow cytometry result of H-2Kb/SIINFEKL tetramer staining of $CD3^+CD8^+$ cells from samples of different treatment groups of in vivo model as in FIG. 5F.

Mature DCs are known to initiate T cell-mediated immune responses. Hence, an induction of cytotoxic T lymphocytes (CTLs) response by the CHME platform in vivo is examined. Circulating peripheral blood mononuclear cells (PBMCs) are analyzed 7 days after in vivo vaccination. Mice immunized with OVA-ELE show an increased percentage of IFN-$\gamma^+$CTLs, resulting in an 18-fold enrichment of IFN-$\gamma^+$CTLs to those of control groups (FIG. 5F). Upon re-stimulation with OVA antigen, the splenocytes collected from OVA-ELE mice secreted much higher levels of IFN-γ than those collected from mice in different control groups (FIG. 5G). Moreover, the presence of SIINFEKL-MHC-I tetramer+$CD8^+$ cells is a 6-fold and 4-fold more in the OVA-ELE group than those in the OVA and IM (10 μg/patch) groups, respectively (FIG. 5I). In addition, a stronger antigen-specific T-cell mediated immune response is observed when the third vaccination is applied. During this process, any cells that express surface antigen are rapidly eliminated by the activated T cells. Furthermore, the OVA-ELE group induces significantly greater lysis efficiency than those of the control groups (FIG. 5H). Meanwhile, all the major organs including the liver, kidney, lung, heart, and spleen remain normal after repeated vaccination using the CHME device. Thus, the result of vaccination with OVA-ELE suggests an improvement of immune response to antigen in vivo by the CHME platform as an alternative way to the commonly used IM injection.

Inhibition of Tumor Growth in In Vivo Tumor Model by CHME Platform

Figure 6A:
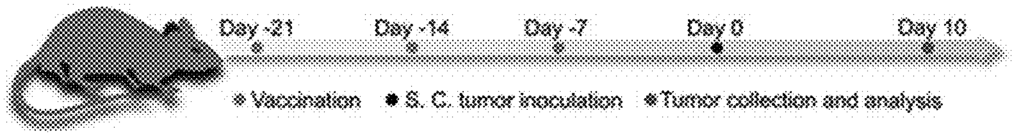
FIG. 6A schematically depicts the scheme of delivering a cancer immunotherapy by the present system to an in vivo cancer model.
Figure 6B:
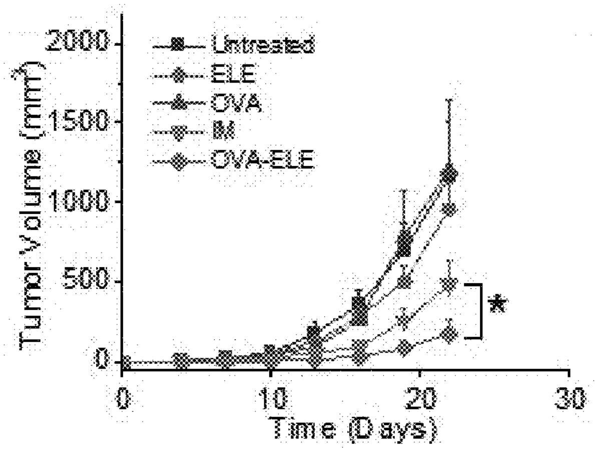
FIG. 6B shows an average tumor growth in the in vivo cancer model immunized under different conditions (untreated, ELE, OVA, IM, OVA-ELE) 7 days before subcutaneous (S.C.) inoculation of OVA-tumor as depicted in FIG. 6A; ELE: micro-electroporation by the present system; IM: intramuscular administration; sample size: n=5; data are presented as means±SEM, * indicates P<0.05, *** indicates P<0.001 by student-t test.
Figure 6C:
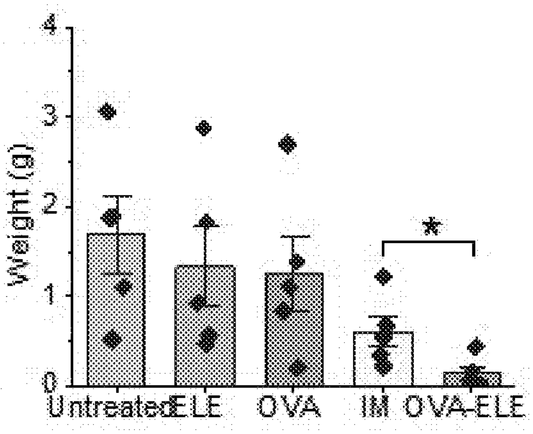
FIG. 6C shows an average tumor mass of the in vivo cancer model immunized under different conditions as in FIG. 6B; sample size: n=5; data are presented as means±SEM, * indicates P<0.05, *** indicates P<0.001 by student-t test.
Figure 6D:
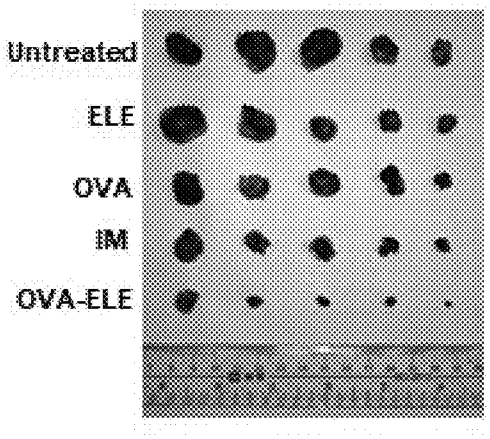
FIG. 6D shows images of some representative tumors obtained from the in vivo cancer model immunized under different conditions as in FIG. 6B.
Figure 6E:
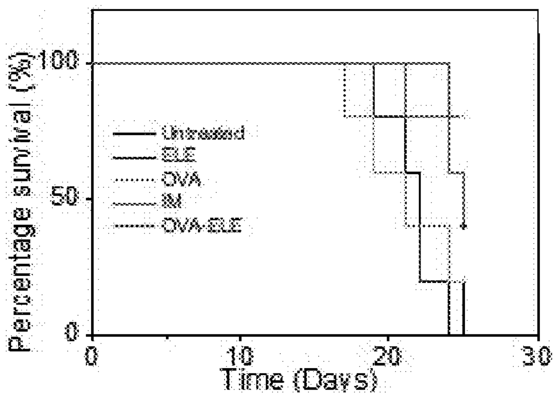
FIG. 6E shows the survival rate of the in vivo cancer model immunized under different conditions as in FIG. 6B over time.
Figure 6F:
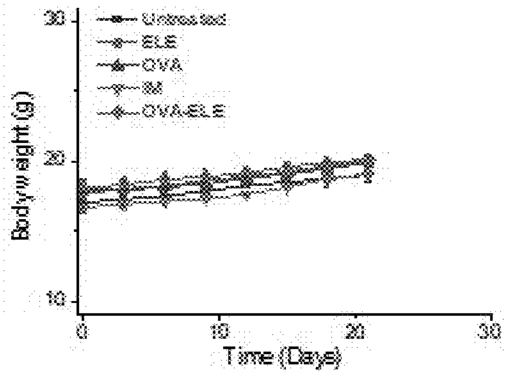
FIG. 6F shows the change in body weight of the in vivo cancer model immunized under different conditions as in FIG. 6B over time; data are presented as means±SEM.

Since the DNA vaccine-encapsulated CHME platform has been shown to induce a good vaccination effect in vivo in the other examples described hereinbefore, it is expected that the CHME platform can also induce antitumor effects on a tumor model if an antitumor agent is encapsulated into and delivered by the CHME platform. In this regard, parallel experiments on OVA-ELE, OVA, ELE, and IM groups in a prophylactic model established by B16-0VA tumor-bearing mice are carried out (FIG. 6A). Healthy C57BL/6 mice are immunized three times using different conditions 7 days before tumor inoculation. 7 days later, mice immunized with OVA-ELE show significant tumor regression. In the OVA-ELE group, the tumor size (395.6±205 $mm^3$ in volume and 0.14±0.08 g in weight) is significantly smaller than those in other groups (FIGS. 6B-6D). For example, a larger tumor size with 830±218.5 $mm^3$ in volume and 0.6±0.17 g in weight are observed in the IM group. As a result, the longevity of mice in the OVA-ELE group is significantly prolonged (FIG. 6E). Meanwhile, the body weight of mice in the OVA-ELE group does not change significantly, which suggests a minimal side effect induced by the CHME platform (FIG. 6F).

Figure 6G:
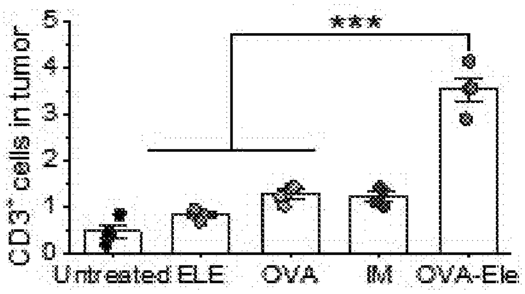
FIG. 6G shows quantitatively T-lymphocyte infiltration among tumor tissues (intertumoral) by the percentage of $CD3^+$ T cells collected from the in vivo cancer model 10 days after final immunization under different conditions as in FIG. 6B; sample size: n=4; data are presented as means±SEM, * indicates P<0.05, *** indicates P<0.001 by student-t test.
Figure 6H:
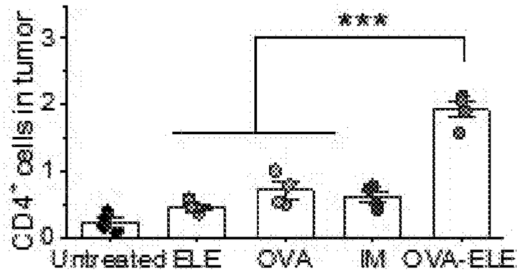
FIG. 6H shows quantitatively intertumoral T-lymphocyte infiltration by the percentage of $CD4^+$ T cells collected from the in vivo cancer model 10 days after final immunization under different conditions as in FIG. 6B; sample size: n=4; data are presented as means±SEM, * indicates P<0.05, *** indicates P<0.001 by student-t test.
Figure 6I:
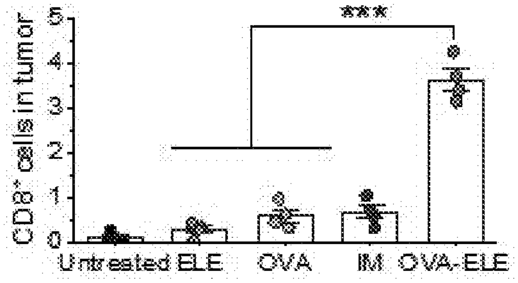
FIG. 6I shows quantitatively intertumoral T-lymphocyte infiltration by the percentage of $CD8^+$ T cells collected from the in vivo cancer model 10 days after final immunization under different conditions as in FIG. 6B; sample size: n=4; data are presented as means±SEM, * indicates P<0.05, *** indicates P<0.001 by student-t test.
Figure 6J:
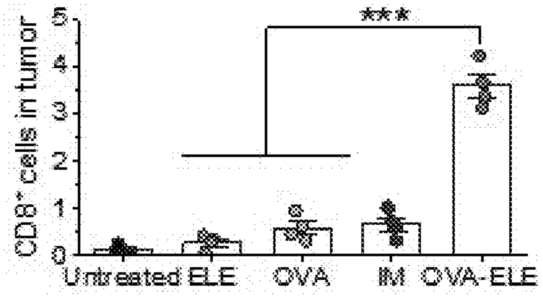
FIG. 6J shows quantitatively intertumoral T-lymphocyte infiltration by the percentage of $CD3^+CD4^+$ T cells collected from the in vivo cancer model 10 days after final immunization under different conditions as in FIG. 6B; sample size: n=4; data are presented as means±SEM, *** indicates P<0.001 by student-t test.
Figure 6K:
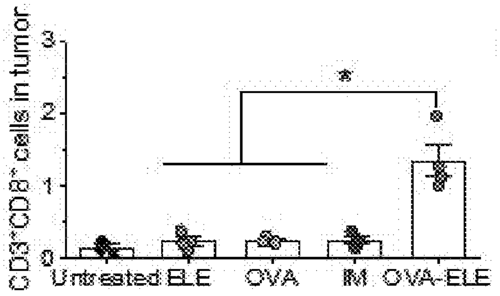
FIG. 6K shows quantitatively intertumoral T-lymphocyte infiltration by the percentage of $CD3^+CD8^+$ T cells collected from the in vivo cancer model 10 days after final immunization under different conditions as in FIG. 6B; sample size: n=4; data are presented as means±SEM, * indicates P<0.05 by student-t test.
Figure 6L:
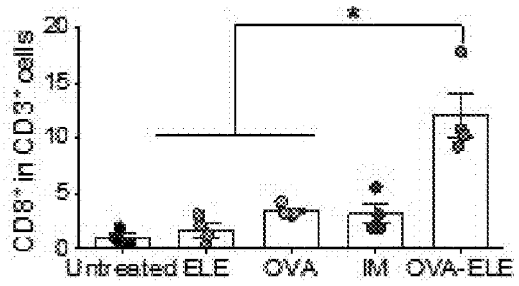
FIG. 6L shows quantitatively expression of CD8 in $CD3^+$ T cells collected from the in vivo cancer model 10 days after final immunization under different conditions as in FIG. 6B; sample size: n=4; data are presented as means±SEM, * indicates P<0.05 by student-t test.
Figure 6M:
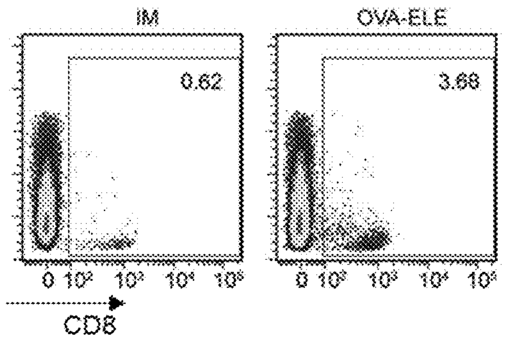
FIG. 6M shows flow cytometry results of $CD8^+$ expression T cells from tumor of the in vivo cancer model with the intramuscular (IM) administration or micro-electroporation of OVA (OVA-ELE) by the present system.

Next, the T-lymphocyte infiltration of tumor tissues (intertumoral) is studied by collecting mice 7 days after different treatments. It is found that the number of tumor-infiltrating lymphocytes (TILs, $CD3^+$ T cells, and $CD4^+$ T cells) increases significantly in tumors treated with OVA-ELE (FIGS. 6G and 6H). About a 25.8-fold increase in $CD8^+$ cells in mice receiving the OVA-ELE is observed compared with untreated mice. In contrast, only a 4.8-fold increase is observed in IM group (FIGS. 6I and 6M). Moreover, the proportion of CTLs (CD3±CD4-CD8±) and effector T cells ($CD3^+CD4^+CD8^-$) within the tumor significantly increases in the OVA-ELE group (FIGS. 6K and 6L). In addition, the percentage of $CD8^+$in $CD3^+$ cells infiltrating the tumor remarkably increases, suggesting that the CHME platform is capable of and effective in delivering antitumor therapy to an animal subject.

Verification of Antitumor Effect Introduced by CHME Platform in Melanoma Model

Figure 7A:
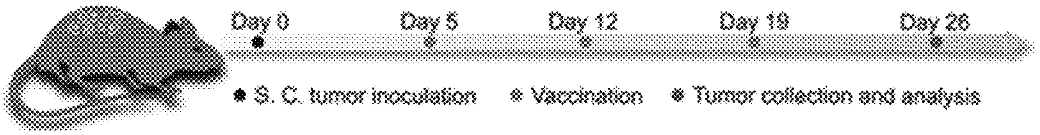
FIG. 7A schematically depicts the scheme of establishing a B16-OVA melanoma tumor model and conducting an antitumor therapeutic effect evaluation of OVA delivered by micro-electroporation of the present system compared to conventional administration method.
Figure 7B:
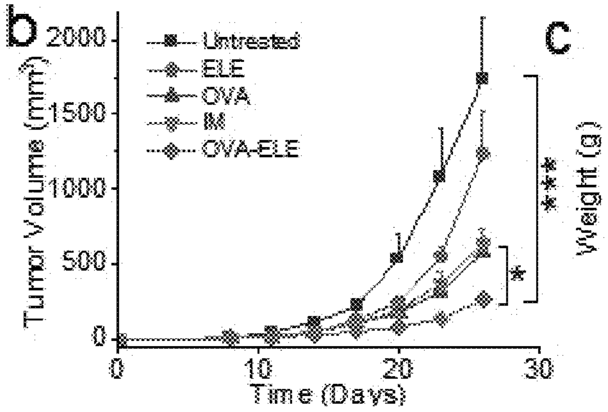
FIG. 7B shows an average tumor growth in the melanoma tumor cancer model immunized under different conditions (untreated, ELE, OVA, IM, OVA-ELE) 7 days before subcutaneous (S.C.) inoculation of OVA-tumor as depicted in FIG. 7A; ELE: micro-electroporation by the present system; IM: intramuscular administration; sample size: n=5; data are presented as means±SEM, * indicates P<0.05, *** indicates P<0.001 by student-t test.
Figure 7C:
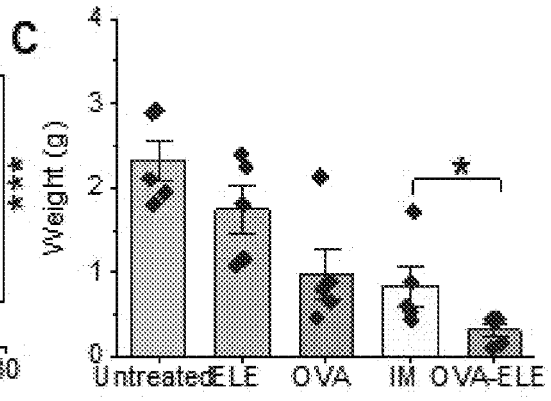
FIG. 7C shows an average tumor mass of the melanoma tumor model immunized under different conditions as in FIG. 7B; sample size: n=5; data are presented as means±SEM, * indicates P<0.05, *** indicates P<0.001 by student-t test.
Figure 7D:
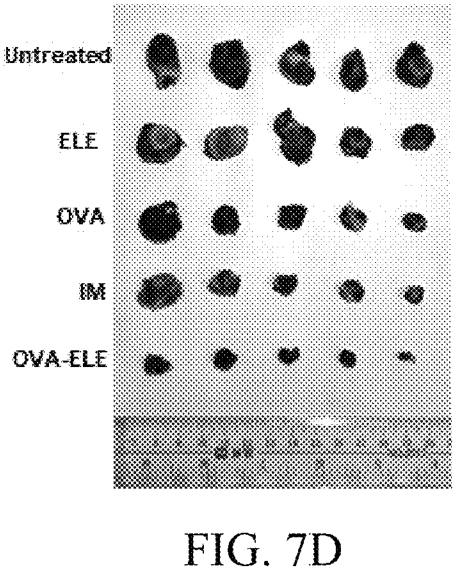
FIG. 7D shows images of some representative tumors obtained from the melanoma tumor model immunized under different conditions as in FIG. 7B.
Figure 7E:
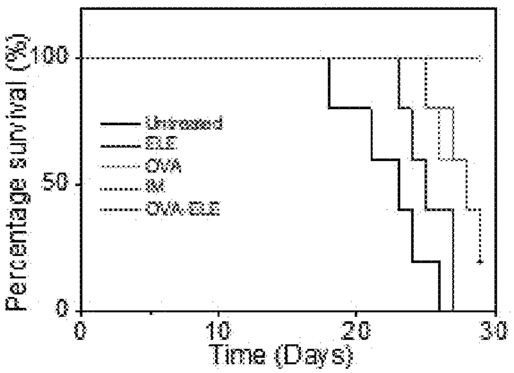
FIG. 7E shows the survival rate of the melanoma tumor model immunized under different conditions as in FIG. 7B over time.
Figure 7F:
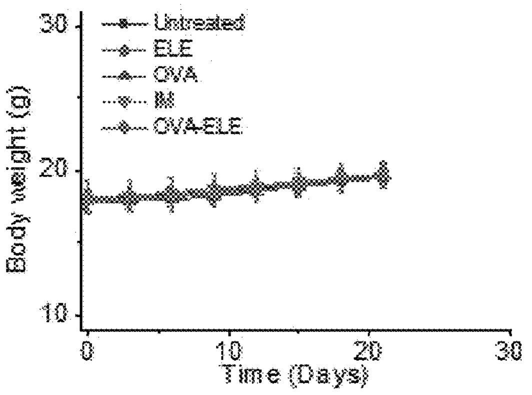
FIG. 7F shows the change in body weight of the melanoma tumor model immunized under different conditions as in FIG. 7B over time; data are presented as means±SEM.
Figure 7G:
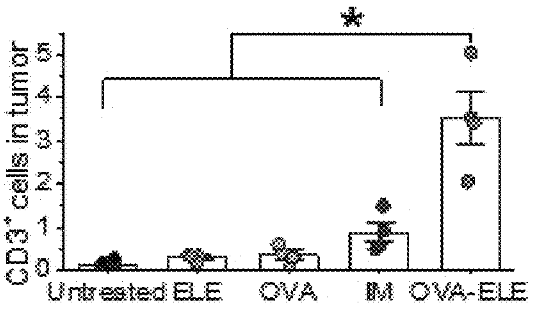
FIG. 7G shows quantitatively T-lymphocyte infiltration among tumor tissues (intertumoral) by the percentage of $CD3^+$ T cells collected from the melanoma tumor model 7 days after immunization under different conditions as in FIG. 7B; sample size: n=4; data are presented as means±SEM, * indicates P<0.05, *** indicates P<0.001 by student-t test.
Figure 7H:
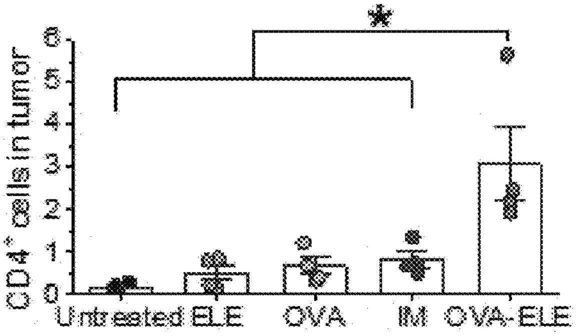
FIG. 7H shows quantitatively intertumoral T-lymphocyte infiltration by the percentage of $CD4^+$ T cells collected from the melanoma tumor model 7 days after immunization under different conditions as in FIG. 7B; sample size: n=4; data are presented as means±SEM, * indicates P<0.05, *** indicates P<0.001 by student-t test.
Figure 7I:
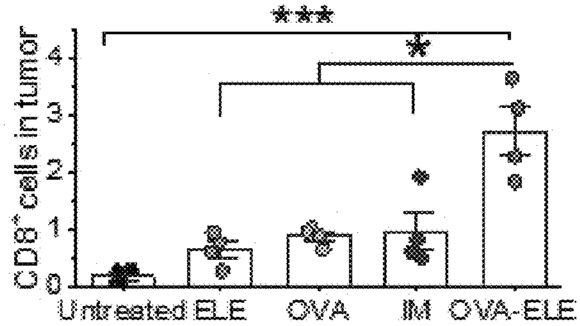
FIG. 7I shows quantitatively intertumoral T-lymphocyte infiltration by the percentage of $CD8^+$ T cells collected from the melanoma tumor model 7 days after immunization under different conditions as in FIG. 6B; sample size: n=4; data are presented as means±SEM, * indicates P<0.05, *** indicates P<0.001 by student-t test.
Figure 7J:
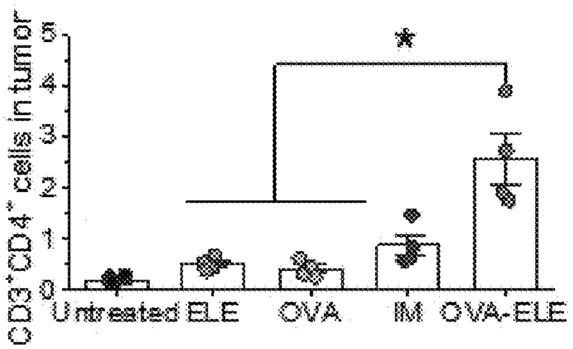
FIG. 7J shows quantitatively intertumoral T-lymphocyte infiltration by the percentage of $CD3^+CD4^+$ T cells collected from the melanoma tumor model 7 days after immunization under different conditions as in FIG. 7B; sample size: n=4; data are presented as means±SEM, * indicates P<0.05, *** indicates P<0.001 by student-t test.
Figure 7K:
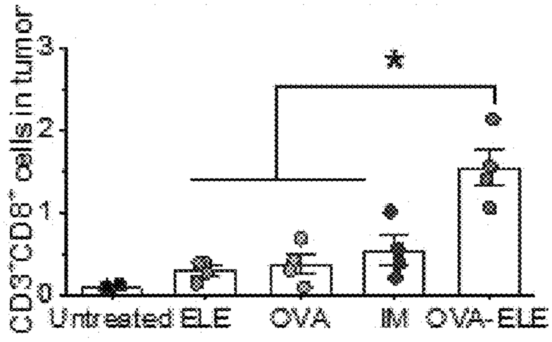
FIG. 7K shows quantitatively intertumoral T-lymphocyte infiltration by the percentage of $CD3^+CD8^+$ T cells collected from the melanoma tumor model 7 days after immunization under different conditions as in FIG. 7B; sample size: n=4; data are presented as means±SEM, * indicates P<0.05, *** indicates P<0.001 by student-t test.
Figure 7L:
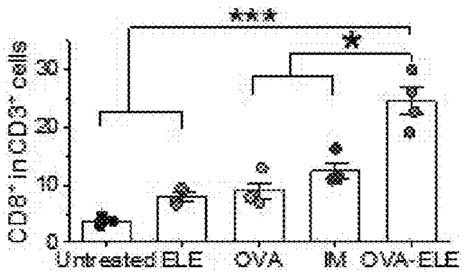
FIG. 7L shows quantitatively expression of CD8 in $CD3^+$ T cells collected from the melanoma tumor model 7 days after immunization under different conditions as in FIG. 7B; sample size: n=4; data are presented as means±SEM, * indicates P<0.05, *** indicates P<0.001 by student-t test.
Figure 7M:
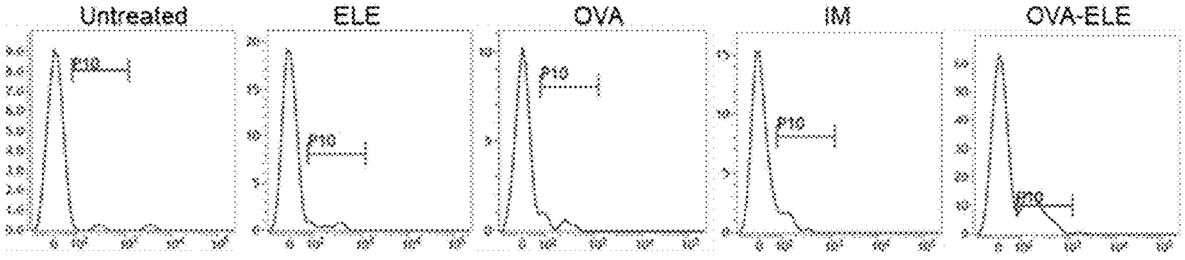
FIG. 7M shows flow cytometry results of CD8 expression in $CD3^+$ T cells from tumor of the in vivo cancer model with different treatments as depicted in FIG. 7B; from the left panel: untreated, ELE, OVA, IM, OVA-ELE.

Similar to the in vivo tests depicted in FIGS. 6A-6M, the therapeutic effect of antitumor agent introduced by the CHME platform is also evaluated in a B16-0VA melanoma tumor model (FIG. 7A). Compared to OVA and IM groups that result in partly delayed tumor growth, OVA-ELE treatment exhibits a stronger inhibitory effect on the tumor growth with the same dose of OVA (FIGS. 7B-7D). As a result, the longevity of mice in the OVA-ELE group is significantly prolonged (FIG. 7E). Importantly, mice treated with OVA-ELE, OVA, ELE, and IM injection show no obvious reduction in body weight, suggesting negligible systemic toxicity (FIG. 7F). To find out the mechanism of anti-tumor effects induced by OVA-ELE treatment, we examined infiltrating T cells in the tumor. The quantitative result shows that the population of infiltrating $CD3^+$, $CD4^+$ and $CD8^+$ T cells in the tumors of the OVA-ELE-treated group is increased by 23.4-, 17.5-, and 15-fold, respectively, compared to those in the untreated group (FIGS. 7G-7I). Also, the percentage of both CD3±$CD8^+$ and CD3±$CD4^+$ T cells within the tumors was significantly increased in the OVA-ELE-treated group (FIGS. 7J-7M). Taken together, by comparing the prophylactic and immune-therapeutic effect between OVA-ELE group and the control group, it is to verify that the OVA-ELE vaccination by the CHME platform exhibits notable tumor inhibition.

Figure 11:
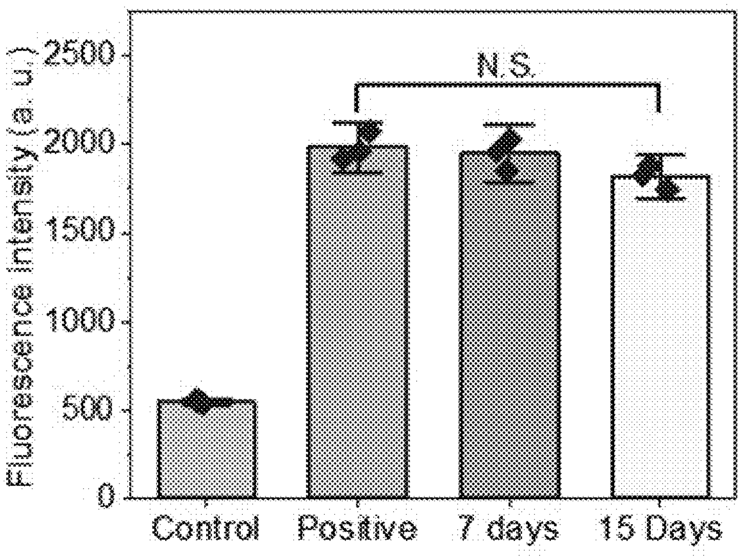
FIG. 11 shows Mean fluorescence intensity showing eGFP expression one day after lipofection transfection of eGFP plasmid released from μEPO device when stored dry at room temperature for 7, 15 days. Data represent the mean±SEM, n=3, N.S., not significant, by student-t test.

In summary, the present disclosure provides a new drug delivery or vaccination system based on a CHME platform. The system benefits from the utilization of electrically conductive microneedles for both biomacromolecules release and in situ electroporation for electro-transfection. The CHME platform allows dry-state storage of vaccines at room temperatures for weeks without loss of activity (FIG. 11), an important advantage for decreasing costs and improving vaccines availability in vaccines storage and long-term transportation. Furthermore, the CHME platform enables a one-step vaccination, avoiding the injection step, rendering it suitable for self-administration or administration by individuals who are minimally trained.

Due to the simple preparation process in which biocompatible PVA and PEDOT:PSS as two major components are mixed through a one-step polymer casting step, the CHME device enables rapid and widespread access to nucleic acid-based vaccination. The PEDOT:PSS is used as a dopant in the hydrogel owing to its good electrical conductivity and electricity-driven release kinetics property. For the electricity-driven release process, the applied negative voltage on the conductive microneedles causes reduction of $PEDOT^+$, which subsequently triggers the release of negatively charged nucleic acids encapsulated in the microneedle through electro-osmosis. In certain embodiments, a working voltage of less than 1 V is sufficient to trigger necessary drug release, suggesting a safe operation for the tissues.

For electroporation manipulation, the CHME platform has an array comprising at least 100 hydrogel electrodes in certain embodiments of the present invention. In comparison to other electroporators with much longer, fewer, and more widely spaced metal electrodes or clamp electrodes that require complex operation procedures or involve high voltage (e.g., 200 V), the present CHME device can induce a stronger electric field at the tips of the microneedles for low-voltage electroporation. In certain embodiments, the CHME device can achieve successful DNA release and electroporation when millisecond pulsed voltages of 30 V and 90 V are employed, respectively. Therefore, the CHME device provides a safer platform for electroporation through the skin, leading to an improved epidermal targeting and reduced nerve interference.

It is also found that the electricity process is critical for the enhanced transfection efficiency, as elimination of electricity almost abrogated such effect. In vitro results showed that the transfection efficiency for CHME was enhanced 10.8-times and 11.5-times higher than the control group without electroporation, for FITC-dextran and eGFP plasmid, respectively. The strategy renders viability of as high as 90% in 3D hydrogel loaded with HEK293T, minimally disturbing the cell's normal functioning and homeostasis, which is particularly beneficial to further clinical applications when applied to therapeutic cells. For example, the human donor-derived T cells could be encapsulated in 3D hydrogel to promote the production of tumor-targeting chimeric antibody receptor (CAR) T cells through our CHME platform.

The in vivo results described in the present disclosure show that the CHME platform can be used to deliver macromolecules into the skin in a highly effective and minimally invasive manner. Additionally, the delivery by the CHME platform does not show any localized or systematic abnormalities or inflammation in various mouse models. Furthermore, volunteers did not report any pain or discomfort when placing the TME on their wrist and applied voltage (FIG. 2C), pending further detailed evaluation of safety in human subjects.

It is also found that, taking an advantage of the enrichment of antigen-presenting cells (APCs) in epidermis and dermis layer, transcutaneous administration of DNA or RNA vaccine is shown to be more effective in stimulating a robust immune response with a significantly lower dose of nucleic acid vaccine than traditional method of muscle injection. Thus, the CHME-delivered OVA plasmid result in a stronger antigen expression, while the control group without electricity elicits very weak transfection. In addition, the CHME platform appears to provide improved capabilities for recruiting a greater number of immune cells and inducing efficient colocalization of DCs and antigen at the treated site, leading to an ultimate strength of immune responses and enhanced DNA immunogenicity. The results of immune response induced by the CHME device described in the present disclosure provide a better insight to apply the CHME device to an enhanced cancer vaccination by loading DNA expressing tumor antigen. As a result, the OVA-ELE group in some examples show superior efficiencies in triggering antitumor immune responses compared to those immunized with OVA, ELE and IM injection. A notable observation from these in vivo studies is a significant increase in the number of SIINFEKLMHC-I tetramer$^+$ CD8α$^+$ T cells in the PBMCs following the single vaccination under the treatment scheme of OVA-ELE. The induction of OVA-specific CTL response is shown to induce cell lysis as measured by an LDH assay in vitro. As a result, the mice of prophylactic models vaccinated under the scheme of OVA-ELE prevent tumor engraftment and cause sustained tumor regression in tumor-bearing mice when compared with mice immunized with OVA, ELE, and IM injection. In addition, the CHME platform is also adaptable in deep-tissue cancer treatment, avoiding limitations resulting from the conventional intratumoral or intranodal injection.

SARS-CoV-2 RBD Circular mRNA Vaccination in In Vivo by the CHME Platform

Figure 8:
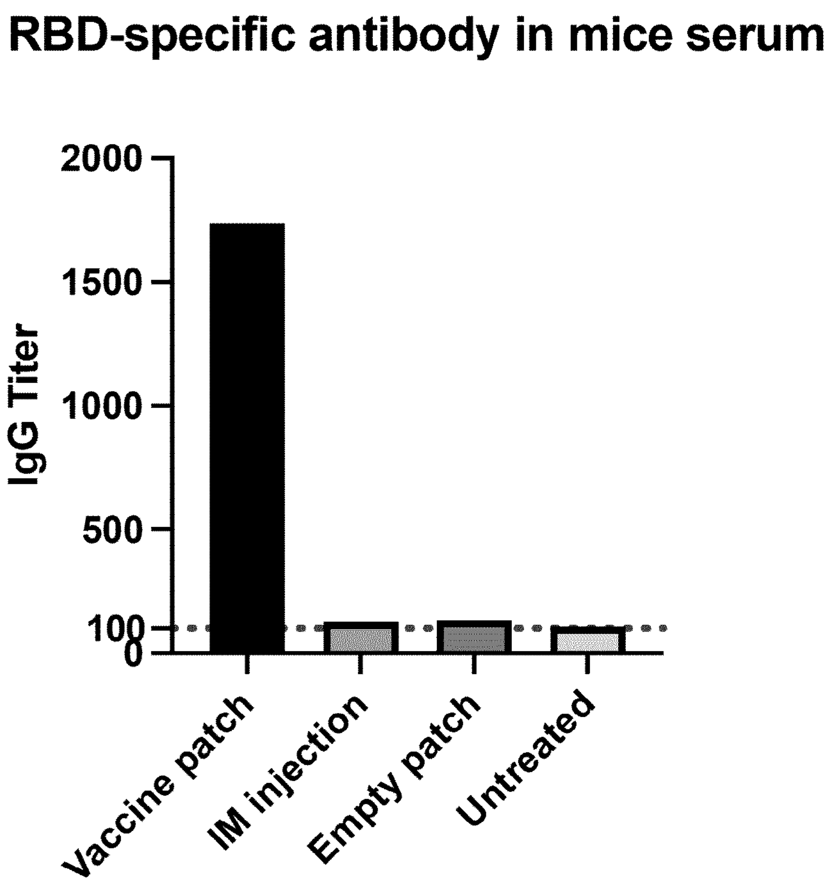
FIG. 8 shows humoral immune response after SARS-CoV-2 receptor-binding domain (RBD) circular mRNA vaccination by the present system under different conditions in in vivo model according to certain embodiments of the present invention.
Figure 9:
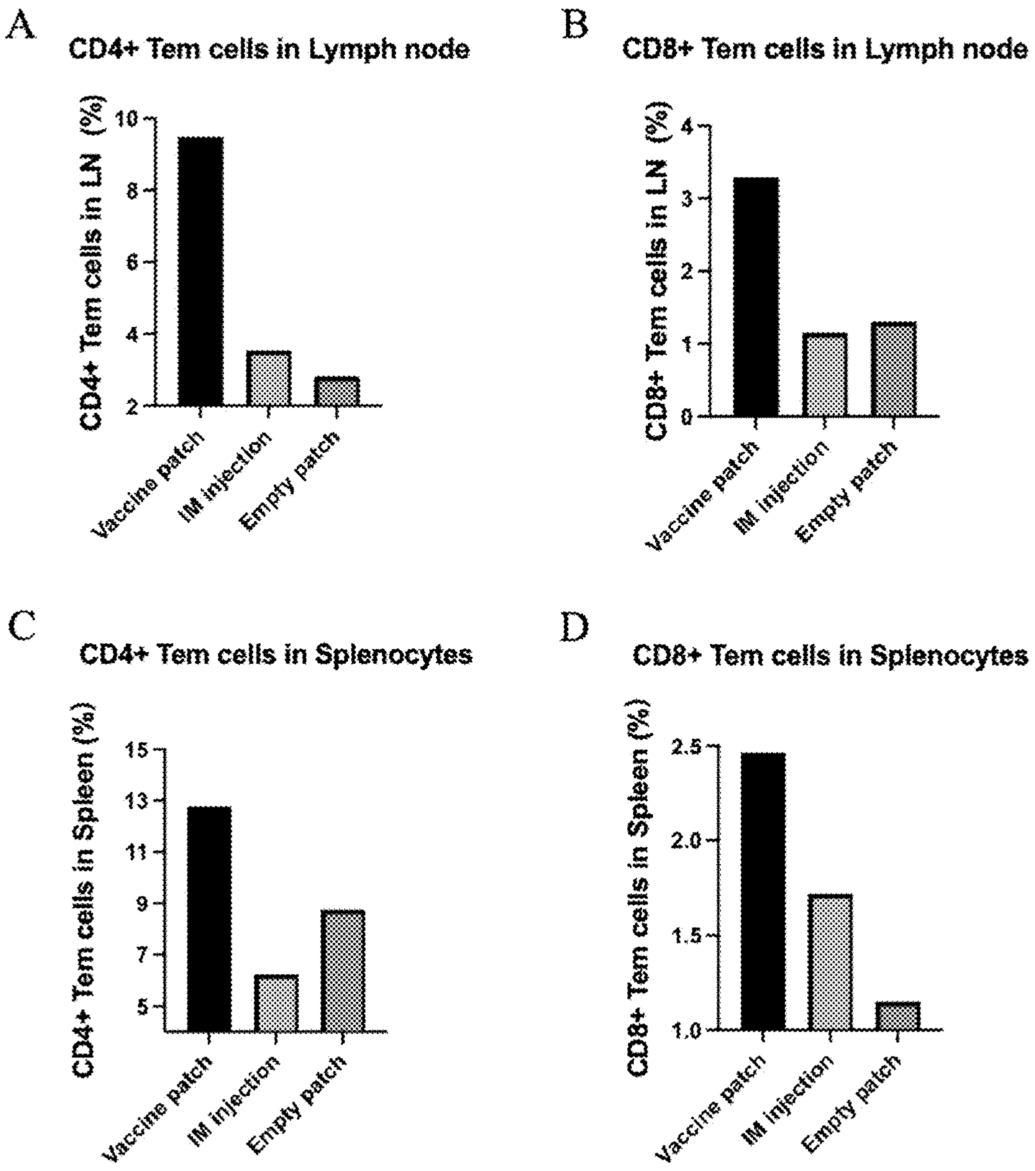
FIG. 9 shows cellular immune response after SARS-CoV-2 RBD circular mRNA vaccination by the present system under different conditions in in vivo model according to certain embodiments of the present invention.

Turning to FIGS. 8 and 9, an in vivo model of SARS-CoV-2 is established in mice to test the immune responses after introducing SARS-CoV-2 receptor binding domain (RBD) circular mRNA vaccines by the CHME platform and other conventional administration methods such as IM injection. In FIG. 8, with the administration of the same amount of mRNA vaccine (10 μg), the highest concentration of RBD-specific antibody is detected in the blood sera of mice administered through the CHME platform versus IM injection after 7 days of administration. Compared to those administrated through IM route, the mice administered through the CHME platform is about 15- to 18-fold higher in terms of the humoral immune response. It is also noteworthy that the efficiency of inducing humoral immune response through the conventional IM injection of the mRNA vaccines is more or less the same as those by the controls (empty patch of CHME microneedles and untreated group), suggesting that the conventional method of mRNA vaccination through IM injection is not an efficient or even a unreliable method of administering mRNA vaccines for inducing RBD-specific antibody in vivo. The present invention, on the other hand, provides a more efficient and reliable platform for inducing antibodies in a subject against the SARS-CoV-2 infection. It is further evidenced by more significant cellular immune responses in the CHME-treated group with the mRNA vaccines than those in IM-treated and empty patch control groups, in terms of the percentage of different memory T-cells (e.g., CD4- and CD8-T cells) in lymphoid (lymph nodes and spleen) obtained on day 7 after administration of the SARS-CoV-2 RBD circular mRNA vaccine (FIG. 9).

Although the invention has been described in terms of certain embodiments, other embodiments apparent to those of ordinary skill in the art are also within the scope of this invention. Accordingly, the scope of the invention is intended to be defined only by the claims which follow.

INDUSTRIAL APPLICABILITY

The present invention not only provides an easy transdermal gene delivery system with high delivery efficiency and minimal invasiveness, but also simplifies the electroporation into a simple, one-step process. From the perspective of basic and clinical researches, efficient gene transfection can be operated with ease in a non-viral mechanism, both in vitro and in vivo. From a clinical application perspective, the present invention provide advantages including low patient discomfort, device manufacturing scalability, no requirements of low temperature storage and transportation, minimal user training, and cost effectiveness. Regarding clinical translation, nucleic acids (DNA vaccine, siRNA, peptide, protein) loaded in the micro-electroporation device of the present system can be changed and optimized not only for personal cancer immunotherapy, but also for various infectious diseases including nucleic acid-based vaccines for MERS, EBOV, Zika, Lassa, and the emerging COVID-19.

REFERENCE

The following literatures are cited herein or relevant to the present invention:

1) Brave, A.; Nystrom, S.; Roos, A. K.; Applequist, S. E. Plasmid DNA Vaccination Using Skin Electroporation Promotes Poly-Functional Cd4 T-Cell Responses. Immunology and Cell Biology 2011, 89, 492-6.
2) Xia, D., Jin, R., Byagathvalli, G., Yu, H., Ye, L., Lu, C. Y., . . . & Prausnitz, M. R. (2021). An ultra-low-cost electroporator with microneedle electrodes (ePatch) for SARS-CoV-2 vaccination. Proceedings of the National Academy of Sciences, 118(45).
3) Glenn, G. M., Taylor, D. N., Li, X., Frankel, S., Montemarano, A., & Alving, C. R. (2000). Transcutaneous immunization: a human vaccine delivery strategy using a patch. Nature medicine, 6(12), 1403-1406.
4) Rouphael, N. G., Paine, M., Mosley, R., Henry, S., McAllister, D. V., Kalluri, H., & Nesheim, W. (2017). The safety, immunogenicity, and acceptability of inactivated influenza vaccine delivered by microneedle patch (TIV-MNP 2015): a randomised, partly blinded, placebo-controlled, phase 1 trial. The Lancet, 390(10095), 649-658.
5) Gill, H. S., Soderholm, J., Prausnitz, M. R., & Sallberg, M. (2010). Cutaneous vaccination using microneedles coated with hepatitis C DNA vaccine. Gene therapy, 17(6), 811-814.
6) Kusama, S., Sato, K., Matsui, Y., Kimura, N., Abe, H., Yoshida, S., & Nishizawa, M. (2021). Transdermal electroosmotic flow generated by a porous microneedle array patch. Nature communications, 12(1), 1-11.

What is claimed is:

1. An electrically conductive and electricity-driven drug delivery system comprising:

an electrically conductive drug delivery device comprising an array of microprotrusions each comprising an electrically conductive component, one or more polymers, and substances or molecules to be delivered to a target site of a recipient when a tip section of each of the microprotrusions contacts a surface of the target site of the recipient under an electrical stimulation, wherein the substances or molecules comprise a nucleic acid or a protein, a peptide, or a fragment thereof; and an electric circuit connecting the electrically conductive drug delivery device to provide an electric potential to the array of the microprotrusions configured to provide a constant negative voltage to induce an electro-osmosis of the substances or molecules to the recipient through a reduction of the electrically conductive component, followed by a millisecond pulse voltage to induce a micro-electroporation for transfection of the nucleic acid at the same array of the microprotrusions.

2. The electrically conductive and electricity-driven drug delivery system of claim 1, wherein the target site is skin of the recipient.

3. The electrically conductive and electricity-driven drug delivery system of claim 1, wherein the array of the microprotrusions comprise microporous structure having an average pore size of about 1 nm to 200 μm.

4. The electrically conductive and electricity-driven drug delivery system of claim 1, wherein the one or more polymers are biocompatible and biodegradable.

5. The electrically conductive and electricity-driven drug delivery system of claim 4, wherein the one or more polymers comprise poly (lactic-co-glycolic acid) (PLGA), poly (glycolic acid) (PGA), poly-L-lactide (PLA), polyvinyl alcohol (PVA), or polyvinylpyrrolidone (PVP).

6. The electrically conductive and electricity-driven drug delivery system of claim 5, wherein the one or more polymers have a concentration of about 0.1 wt. % to 60 wt. % in the array of the microprotrusions.

7. The electrically conductive and electricity-driven drug delivery system of claim 1, wherein the electrically conductive component comprises one or more of PEDOT: PSS, polythiophene (PTh), carbon nano tube, polypyrrole (PPy), polyaniline, and Mxene.

8. The electrically conductive and electricity-driven drug delivery system of claim 1, wherein the electrically conductive component is in a concentration of about 0.1 wt. % to 90 wt. % in the array of the microprotrusions.

9. The electrically conductive and electricity-driven drug delivery system of claim 1, wherein the nucleic acid is a nucleic acid-based vaccine comprising a DNA or RNA vaccine, wherein the RNA vaccine comprises a linear or circular mRNA vaccine, and wherein the DNA vaccine comprises a DNA plasmid capable of expressing one or more antigenic proteins in the recipient.

10. The electrically conductive and electricity-driven drug delivery system of claim 1, wherein the nucleic acid is loaded into each of the microprotrusions at a weight of about 1 pg to 100 g.

11. The electrically conductive and electricity-driven drug delivery system of claim 1, wherein the electric circuit comprises a negative electrode, a connection between the negative electrode and the electrically conductive drug delivery device, and a power supply.

12. The electrically conductive and electricity-driven drug delivery system of claim 11, wherein the negative electrode comprises one or more conductive materials of copper, silver, iron, tin and aluminum.

13. The electrically conductive and electricity-driven drug delivery system of claim 11, wherein the connection is a pair of magnetic clips for securing the electrically conductive drug delivery device to the negative electrode.

14. The electrically conductive and electricity-driven drug delivery system of claim 11, wherein the power supply connects to the negative electrode and the electrically conductive drug delivery device, respectively, to provide the electric potential from 1 nV to 500 V or the electric potential of a pulse voltage from 1 mV to 200 V at a pulse duration from about 1 ms to 10 s, or to provide an electric current by the electric potential from 1 nA to 500 A.

15. A method for delivering substances or molecules to the target site of the recipient based on the micro-electroporation and the electro-osmosis, the method comprising:

providing the electrically conductive and electricity-driven drug delivery system of claim 1;

contacting the tip section of the array of the microprotrusions with the surface of the target site of the recipient;

triggering release of the substances or molecules from the tip section of the array of the microprotrusions by the electro-osmosis to the target site through a reduction of conductive component of the microprotrusions under the constant negative voltage provided by the electric circuit; and initiating the micro-electroporation for the transfection of the nucleic acid under the millisecond pulse voltage provided by the electric circuit at the same tip section of the array of the microprotrusions.

16. The method of claim 15, wherein the constant negative voltage or the millisecond pulse voltage is the electric potential from 1 nV to 500 V or the electric potential of a pulse voltage from 1 mV to 200 V at a pulse duration from about 1 ms to 10 S.

17. The method of claim 15, wherein the target site of the recipient comprises 3D cultured cell hydrogel bulk, and wherein the 3D cultured cell hydrogel bulk comprises one or more of gelatin-based hydrogel, alginate-based hydrogel, chitosan-based hydrogel, and PEG-based hydrogel.

18. The method of claim 15, wherein the target site of the recipient comprises skin, oral mucous membrane, gastrointestinal mucosa membrane, or external or internal mucosa membrane of organs, and wherein the recipient is a mouse, a rat, a pig, a rabbit, a frog, a cattle, a horse, a non-human primate animal, or a human.

19. A method for fabricating the electrically conductive and electricity-driven drug delivery system of claim 1, comprising:

preparing a conductive polymer composition for forming the electrically conductive drug delivery device;

providing a mold with multiple cavities corresponding to shape and dimension of the microprotrusions of the electrically conductive drug delivery device;

casting the conductive polymer composition into the mold until the conductive polymer composition is set to form the array of the microprotrusions;

demolding the array of microprotrusions from the mold and securing thereof to a negative electrode of the electric circuit;

said preparing the conductive polymer composition comprising:

mixing a polymer with a conductive component to form a precursor solution; and adding the substances or molecules into the precursor solution, the polymer comprising one or more biocompatible and biodegradable polymers of poly (lactic-co-glycolic acid) (PLGA), poly (glycolic acid) (PGA), poly-L-lactide (PLA), polyvinyl alcohol (PVA), or polyvinylpyrrolidone (PVP) in a concentration of about 0.1 wt. % to 60 wt. %;

the conductive component comprising one or more of PEDOT: PSS, polythiophene (PTh), carbon nano tube, polypyrrole (PPy), polyaniline, and Mxene in a concentration of about 0.1 wt. % to 90 wt. %;

the substances or molecules comprising a nucleic acid and biomacromolecules in the absence of carrier at a weight of about 1 μg to 100 g per microprotrusion;

the array of microprotrusions comprising a microporous structure with an average pore size of about 1 nm to 200 μm, and having an average conductivity of about 1.2 to 2.7 S/m and an average failure force of about 0.4 N per microprotrusion.

20. The method of claim 19, wherein the biomacromolecules comprise proteins and peptides, or any fragment thereof.

* * * * *